US007070940B2

(12) United States Patent
Corti et al.

(10) Patent No.: US 7,070,940 B2
(45) Date of Patent: Jul. 4, 2006

(54) METHOD FOR DETERMINING THE ABILITY OF A COMPOUND TO MODIFY THE INTERACTION BETWEEN PARKIN AND THE P38 PROTEIN

(75) Inventors: Olga Corti, Paris (FR); Cornelia Hampe, Triel sur Seine (FR); Alexis Brice, Paris (FR); Laurent Pradier, Verrieres (FR); Thomas Rooney, Orsay (FR); Alain Fournier, Chatenay Malabry (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/622,817

(22) Filed: Jul. 18, 2003

(65) Prior Publication Data

US 2004/0214763 A1 Oct. 28, 2004

Related U.S. Application Data

(60) Provisional application No. 60/396,929, filed on Jul. 18, 2002.

(51) Int. Cl.
*G01N 33/53* (2006.01)
*C07K 14/00* (2006.01)

(52) U.S. Cl. .................................. 435/7.1; 530/350
(58) Field of Classification Search ................ 435/7.1; 530/350
See application file for complete search history.

(56) References Cited

U.S. PATENT DOCUMENTS 5,843,757 A * 12/1998 Vogelstein et al. ........ 435/252.3
6,010,856 A * 1/2000 Ulevitch et al. ................ 435/6
6,716,621 B1 * 4/2004 Shimizu et al. .......... 435/320.1

OTHER PUBLICATIONS

Cohen 1997; Trends in Cell Biology 7:353-361.*
Abbas, Nacer et al., A wide variety of mutations in the parkin gene are responsible for autosomal recessive parkinsonism in Europe, Human Molecular Genetics, (1999), vol. 8, No. 4, pp. 567-574.
Altschul Stephen F. et al., Basic Local Alignment Search Tool, Journal Molecular Biology, (1990), vol. 215, pp. 403-410.
Altschul Stephen F. et al., Gapped BLAST And PSI-BLAST: A New Generation Of Protein Database Search Programs, Nucleic Acids Research, (1997), vol. 25, No. 17, pp. 3389-3402.
C.B. Lucking et al., Homozygous deletions in parkin gene in European and North African families with autosomal recessive juvenile parkinsonism, The Lancet, vol. 352, Oct. 24, 1998, pp. 1355-1356.

E. Leroy et al., The ubiquitin pathway in Parkinson's disease, Nature, vol. 395, Oct. 1, 1998, pp. 451-452.
E. Morett et al., A novel transactivation domain in parkin, Trends in Biochem Sci., vol. 24, Jun. 1999, pp. 229-231.
H. Shimura et al., Familial Parkinson disease gene product, parkin, is a ubiquitin-protein ligase, Nature Genetics, vol. 25, Jul. 2000, pp. 302-305.
H. Shimura et al., Immunohistochemical and Subcellular Localization of Parkin Protein: Absence of Protein in Autosomal Recessive Juvenile Parkinsonism Patients, Ann. Neurol. vol. 45, 1999, pp. 668-672.
M. Polymeropoulos et al., Mutation in the alpha-synuclein gene identified in families with Parkinson's Disease, Science, vol. 276, Jun. 27, 1997, pp. 2045-2047.
N. Hattori et al., Molecular Genetic Analysis of a Novel Parkin Gene in Japanese Families with Autosomal Recessive Juvenile Parkinsonism: Evidence for Variable Homozygous Deletions in the Parkin Gene in Affected Individuals, Annals of Neurology, vol. 44, Issue 3, 1998, pp. 935-941.
R. Kopito, Aggresomes, inclusion bodies and protein aggregation, Trends in Cell Biology, vol. 10, Dec. 2000, pp. 524-530.
R.K. Brachmann et al., Tag games in yeast: the two-hybrid system and beyond, Current Opinion Biotechnol. vol. 8, No. 5, Oct. 1997, pp. 561-568.
S. Fields et al., A novel genetic system to detect protein—protein interactions, Nature, vol. 340, Jul. 20, 1989, pp. 245-246.
S. Quevillon et al., Macromolecular Assemblage of Aminoacyl-tRNA Synthetases: Identification of Protein-Protein Interactions and Characterization of a Core Protein, J. Mol. Biol. vol. 285, 1999, pp. 183-195.
Sanger et al., DNA sequencing with chain-terminating inhibitors, Proc. Natl. Acad. Sci. 74(12), 5463-5467 (1977).
T. Kitada et al., Mutations in the parkin gene cause autosomal recessive juvenile parkinsonism, Nature, vol. 392, Apr. 9, 1998, pp. 605-608.
T.R. Flotte et al., Gene Expression from Adeno-associated Virus Vectors in Airway Epithelial Cells, Am. J. Respir. Cell Mol. Biol., vol. 7, 1992, pp. 349-356.
Y. Imai et al., Parkin Suppresses Unfolded Protein Stress-induced Cell Death through its E3 Ubiquitin-protein Ligase Activity, Journ. of Biol. Chem., vol. 275, No. 46, Nov. 17, 2000, pp. 35661-35664.
Y. Sunada et al., Differential expression of the parkin gene in the human brain and peripheral leukocytes, Neuroscience Letters, vol. 254, pp. 180-182.

* cited by examiner

*Primary Examiner*—Karen Cochrane Carlson
(74) *Attorney, Agent, or Firm*—Karen I. Krupen

(57) ABSTRACT

The present invention relates to a method for determining the ability of a compound to modify the interaction between parkin and the p38 protein, and in particular to a method for screening for or detecting compounds intended for the prevention and/or treatment of neurodegenerative pathological conditions. The present inventions also relates to compounds identified in the above screening method.

6 Claims, 7 Drawing Sheets

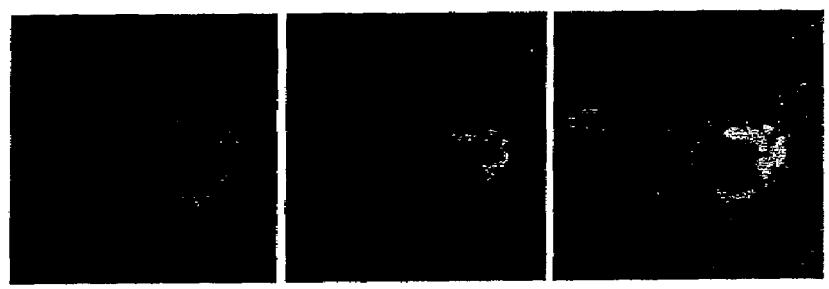
FIG 4A Parkine-Ubi-  FIG 4B p38  FIG 4C superposition
COS7
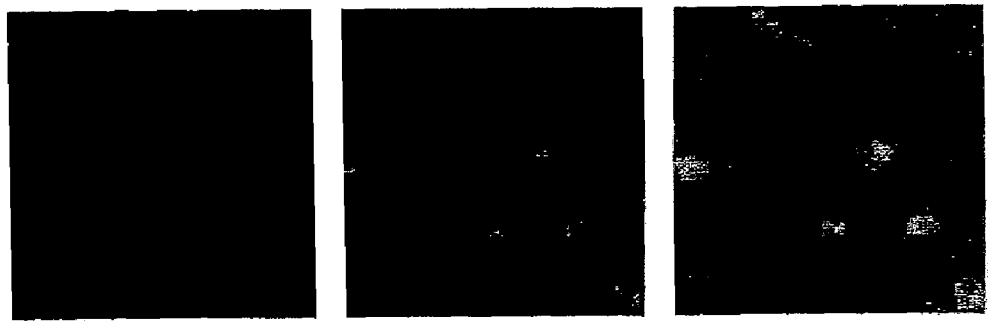
FIG 4D  FIG 4E  FIG 4F

METHOD FOR DETERMINING THE ABILITY OF A COMPOUND TO MODIFY THE INTERACTION BETWEEN PARKIN AND THE P38 PROTEIN

CROSS-REFERENCE TO RELATED APPLICATIONS

This application claims benefit of U.S. Provisional Application No. 60/396,929, filed Jul. 18, 2002 and priority of Great Britain Application No. 0229934.5, filed Dec. 20, 2002.

BACKGROUND OF THE INVENTION

1. Field of the Invention

The present invention relates to a method for determining the ability of a compound to modify the interaction between parkin and the p38 protein, and in particular a method for screening for or detecting compounds intended for the prevention and/or treatment of neurodegenerative pathological conditions.

It also relates to compounds intended for the prevention and/or treatment of neurodegenerative pathological conditions which may modify the interaction between parkin and the p38 protein.

2. Description of the Related Art

The parkin gene is mutated in certain familial forms (autosomal recessive juvenile forms) of Parkinson's disease (Kitada et al., 1998). Parkinson's disease (Lewy, 1912) is one of the most common neurodegenerative diseases, affecting more than 1% of the population over 55 years of age. Patients suffering from this disease have neurological disorders which are grouped together under the term Parkinson's Syndrome, characterized by a rigidity, bradykinesia, and shaking while resting. These symptoms are the consequence of a degeneration of the dopaminergic neurons of the substantia nigra of the brain.

Most patients suffering from Parkinson's disease do not have a family history. However, some of the familial cases correspond to a monogenic form of the disease. At the present time, only three different genes have been identified in certain rare hereditary forms. The first form corresponds to an autosomal dominant form, in which the gene responsible encodes alpha synuclein (Polymeropoulos et al., 1997). This protein is an abundant constituent of the intracytoplasmic inclusions called Lewy bodies, which are used as a marker for Parkinson's disease (Lewy, 1912). The second form, also autosomal dominant, is associated with a mutation in a gene encoding a hydrolase called ubiquitin carboxy-terminal hydrolase Li (Leroy et al., 1998). This enzyme is presumed to hydrolyse ubiquitin polymers or conjugates to ubiquitin monomers. The third form differs from the previous forms in that it has an autosomal recessive transmission and often begins before 40 years of age, and also in that there is an absence of Lewy bodies. These diseases respond more favourably to levodopa, a dopamine precursor which is used as treatment for Parkinson's disease. The gene involved in this form encodes a novel protein called parkin (Kitada et al., 1998).

The parkin gene consists of 12 exons which cover a genomic region of more than 500 000 base pairs on chromosome 6 (6q25.2-q27). At the present time, two major types of mutation of this gene, which are the cause of the disease, are known, either deletions of varying size in the region which covers exons 2 to 9, or point mutations which produce the premature appearance of a stop codon or a change of amino acid (Kitada et al., 1998; Abbas et al., 1999; Lucking et al., 1998; Hattori et al., 1998). The nature of these mutations and the autosomal recessive method of transmission suggests a loss of function of parkin, leading to Parkinson's disease.

This gene is expressed in a large number of tissues, and in particular in the substantia nigra. Several transcripts corresponding to this gene exist, which originate from different alternative splicings (Kitada et al., 1998; Sunada et al., 1998). In the brain, two types of messenger RNA are found, of which one lacks the portion corresponding to exon 5. In leukocytes, parkin messenger RNAs which do not contain the region encoding exons 3, 4 and 5 have been identified. The longest of the parkin messenger RNAs, which is present in the brain, contains 2 960 bases and encodes a 465 amino acid protein.

This protein has weak homology, in its N-terminal portion, with ubiquitin. Its C-terminal half contains two ring finger motifs, separated by an IBR (In Between Ring) domain, corresponding to a cysteine-rich region able to bind metals, like the zinc finger domains (Morett, 1999). It has been shown, by immunocytochemistry, that parkin is located in the cytoplasm and the Golgi apparatus of neurons of the substantia nigra which contain melanin (Shimura et al., 1999). In addition, this protein is present in certain Lewy bodies of Parkinsonians. Recent studies indicate that parkin functions like E3 ubiquitin-protein ligase: an enzyme which is thought to facilitate the transfer of ubiquitin from a protein called E2 ubiquitin-conjugating enzyme to target proteins called upon to be degraded by a proteasome-dependent process (Shimura et al., 2000). One hypothesis would be that parkin has a protective role against the accumulation of incorrectly conformed proteins coming from the endoplasmic reticulum which, if not degraded, would induce a neurotoxic stress leading to neuronal death (Imai et al., 2000). In the autosomal recessive juvenile forms, parkin is absent, thus confirming that the loss of this function is responsible for the disease.

Elucidation of the exact role of the parkin protein in the process of degeneration of dopaminergic neurons is therefore determinant for the understanding of and the therapeutic approach to Parkinson's disease, and more generally diseases of the central nervous system.

In addition, in terms of the discovery of novel molecules for treating Parkinson's disease, and in general diverse neurodegenerative diseases, the stakes are high for public health. This is because there is, however, no specific screening method for such molecules which can be used at high throughput.

BRIEF SUMMARY OF THE INVENTION

The applicants have therefore endeavored to implement a rapid, specific and effective screening test for molecules treating Parkinson's disease, and in general diverse neurodegenerative diseases.

They have shown, surprisingly, that parkin interacts, at the level of its central region, with the p38 protein, a protein known to be a structural component of the multiprotein complexes of aminoacyl-tRNA synthase.

They have also demonstrated that the p38 protein is ubiquitinylated by parkin.

A first subject of the present invention is therefore a method for screening for or detecting compounds intended for the prevention and/or treatment of neurodegenerative pathological conditions, comprising the steps consisting in:

bringing said compound into contact with parkin and the p38 protein, or parts or homologues of these proteins, or cells or cell fragments or cell lysates comprising such proteins and, optionally, a suitable enzyme substrate, and measuring the ability of said compound to modify the interaction between parkin and the p38 protein, or parts of these proteins.

It also relates to a method for screening for or detecting compounds intended for the prevention and/or treatment of neurodegenerative pathological conditions, comprising the steps consisting in:

bringing said compound into contact with the p38 protein, or a part or a homologue of this protein, or cells or cell fragments or cell lysates comprising such a protein and, optionally, a suitable enzyme substrate, and measuring the binding of said compound to the p38 protein.

A subject of the invention is also a method for determining the binding of a compound to the p38 protein, comprising the steps consisting in:

bringing said compound into contact with the p38 protein, or a part or a homologue of this protein, or cells or cell fragments or cell lysates comprising such a protein and, optionally, a suitable enzyme substrate, and measuring the binding of said compound to the p38 protein.

A subject of the invention is also a method for determining the ability of a compound to modify the interaction between parkin and the p38 protein, comprising the steps consisting in:

bringing said compound into contact with parkin and the p38 protein, or parts or homologues of these proteins, or cells or cell fragments or cell lysates comprising such proteins and, optionally, a suitable enzyme substrate, and measuring the ability of said compound to modify the interaction between parkin and the p38 protein.

A subject of the invention is also a method of curative or preventive treatment of neurodegenerative diseases, comprising the steps:

of selecting said compound using a method consisting in:
bringing said compound into contact with the p38 protein, or a part or a homologue of this protein, or cells or cell fragments or cell lysates comprising such a protein and, optionally, a suitable enzyme substrate, and measuring the binding of said compound to the p38 protein, and of administering said compound to a patient suffering from said disease.

It also relates to a method of curative or preventive treatment of neurodegenerative diseases, comprising the steps:

of selecting said compound using a method consisting in:
bringing said compound into contact with parkin and the p38 protein, or parts or homologues of these proteins, or cells or cell fragments or cell lysates comprising such proteins and, optionally, a suitable enzyme substrate, and measuring the ability of said compound to modify the interaction between parkin and the p38 protein, and of administering said compound to a patient suffering from said disease.

These methods may be used in vitro or in vivo.

Advantageously, the property or properties of fluorescence transfer is (are) used when these methods are used in vitro.

Thus, according to a preferential embodiment, the interaction between parkin and p38 is measured using HTRF (Homogeneous Time Resolved Fluorescence) technology. This technology has been described by Mathis (1995 and 1999).

DESCRIPTION OF THE DRAWINGS

FIGS. 4A to 4L illustrate the co-localization of parkin and of the p38 protein in mammalian cells. COS-7 (FIGS. 4A to 4F), PC-12 (FIGS. 4G to 4I) and SH-SY5Y (FIGS. 4J to 4L) cells were cotransfected with the vectors pcDNA3-HA-Parkin-Ubi (FIGS. 4A to 4C) or pcDNA3-HA-Parkin (FIGS. 4D to 4L), and the vector pcDNA3-myc-P38 (FIGS. 4A to 4L); 48 h later, they were fixed and then incubated with the anti-myc monoclonal antibody and the Asp5 polyclonal antibody. The cells were analysed by confocal microscopy. The fluorescence corresponding to the parkin is demonstrated on FIGS. 4A, 4D, 4G and 4J. The fluorescence corresponding to the p38 is demonstrated on FIGS. 4B, 4E, 4H and 4K. FIGS. 4C, 4F, 4I and 4L correspond to the superposition of the two fluorescences.

FIG. 6A illustrates the situation when there is interaction between parkin and p38, whereas the absence of interaction is illustrated in FIG. 6B.

DETAILED DESCRIPTION OF THE INVENTION

Figure 1:
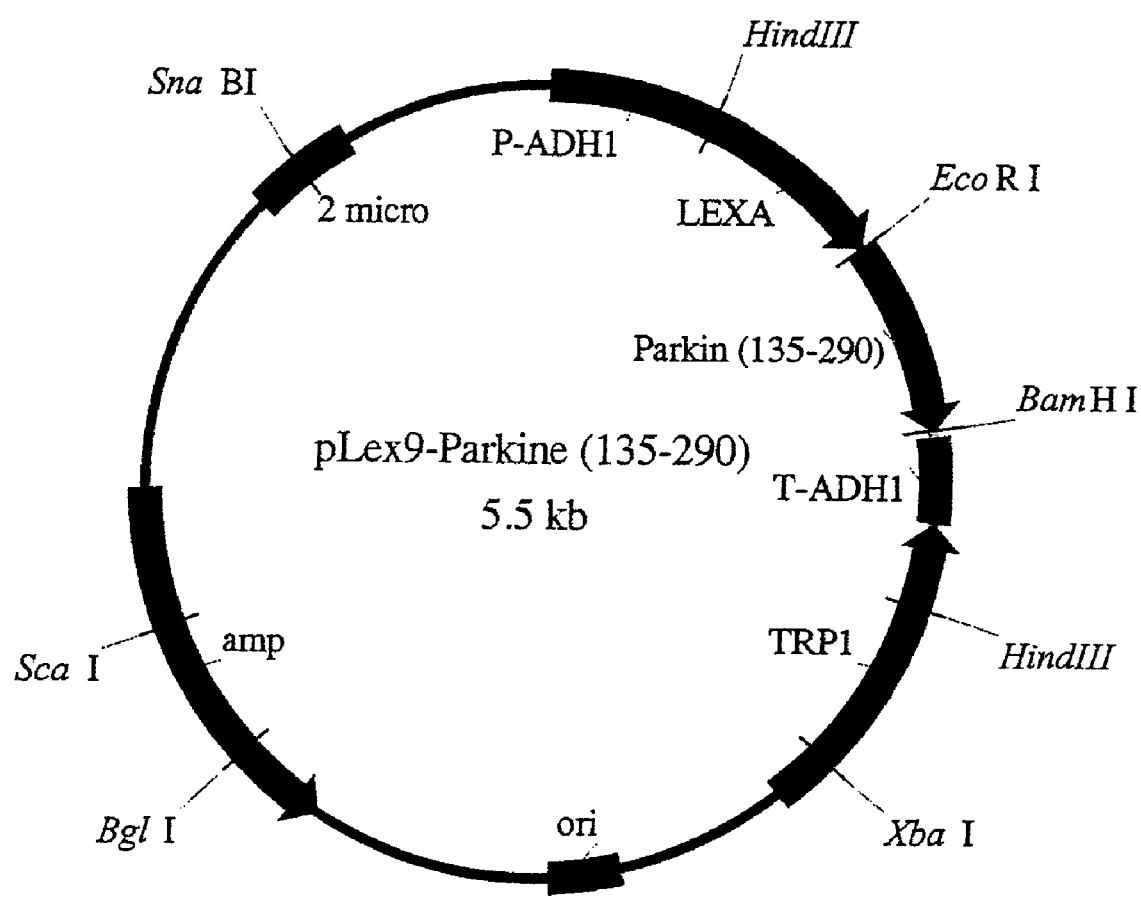
FIG. 1 is a representation of the vector pLex9-Parkin (135–290).

In vivo, use is preferentially made of yeasts expressing the p38 proteins and parkin, or parts or homologues of these proteins, fused respectively to the bacterial repressor LexA or to the DNA-binding domain of yeast GAL4 and to the transactivation domain of the yeast GAL4 protein. Interaction of the p38 protein with parkin makes it possible to reconstitute a transactivator which induces expression of a reporter gene placed under the control of a promoter having a regulatory sequence to which attaches the LexA protein or the DNA-binding domain of GAL4, respectively, according to the principle of the two-hybrid method (Fields and Song, 1989). Thus, according to a preferential embodiment, a reporter gene will be chosen which encodes a protein which allows growth of yeast under conditions where this growth is inhibited when there is no expression of said reporter gene. This reporter gene will, for example, be an auxotrophic gene encoding an enzyme involved in a biosynthetic pathway for amino acids or nitrogenous bases, such as the yeast genes URA3, ADE2, HIS3, etc., or equivalent genes originating from other organisms. Thus, when the interaction between P38 and parkin, or parts or homologues of these proteins, expressed in this system is inhibited or attenuated by a natural or synthetic chemical compound, the reporter gene will not be expressed or will be less well expressed, thus inducing arrest or slowing down of yeast growth under the conditions previously described. This effect may be visible to the naked eye or via devices for measuring yeast growth which are known to those skilled in the art. Even more preferentially, a reporter gene will be used which induces, when it is expressed, inhibition of yeast growth under conditions where expression of this gene is toxic and according to the principle of the reverse two-hybrid method (Brachmann and Boeke, 1997). This reporter gene may be the yeast URA3 gene, or an equivalent gene originating from other organisms, which, when it is expressed, prevents the growth of yeasts cultured in the presence of 5-fluoroorotic acid. In the presence of the URA3 gene product: orotate decarboxylase, 5-fluoroorotic acid is metabolized to a product which is toxic for yeast. Thus, when the interaction between P38 and parkin, or parts or homologues of these proteins, expressed in this system, is inhibited or attenuated by a natural or synthetic chemical compound, the reporter gene will not be expressed or will be less well expressed, thus inducing yeast growth in the presence of 5-fluoroorotic acid. This effect may be visible to the naked eye or via devices for measuring yeast growth which are known to those skilled in the art.

Preferentially, the p38 protein, or a part or a homologue of this protein, is expressed from one of the nucleotide sequences SEQ ID NO:1 or SEQ ID NO:4, or from a sequence exhibiting at least 65%, preferentially at least 75%, and even more preferentially at least 85% or 95% identity with one of these sequences.

Thus, the p38 protein, or a part or a homologue of this protein, may have one of the sequences SEQ ID NO:2 or SEQ ID NO:5, or a sequence exhibiting at least 65%, preferentially at least 75%, and even more preferentially at least 85% or 95% identity with one of these sequences.

According to a preferential embodiment, the parkin, or a part or a homologue of this protein, is expressed from one of the nucleotide sequences, SEQ ID NO:7 or SEQ ID NO:10, or from a sequence exhibiting at least 65%, preferentially at least 75%, and even more preferentially at least 85% or 95% identity with one of these sequences.

The parkin, or a part or a homologue of this protein, may have the sequences SEQ ID NO:8, or a sequence exhibiting at least 65%, preferentially at least 75%, and even more preferentially at least 85% or 95% identity with one of these sequences.

Parkin variants may also be used to implement the present invention. Such variants may be those described in PCT application WO 00/31253.

Advantageously, the parkin is the human isoform of sequence SEQ ID NO:8.

Preferentially, the p38 protein is the human isoform of sequence SEQ ID NO:2.

They may also be any other isoforms of these proteins.

The present invention also relates to the use of compounds selected using a method consisting in:

bringing said compound into contact with parkin and the p38 protein, or parts or homologues of these proteins, or cells or fragments or lysates and, optionally, a suitable enzyme substrate, and measuring the ability of said compound to modify the interaction between parkin and the p38 protein, for producing a medicinal product for the curative or preventive treatment of neurodegenerative diseases.

The present invention also relates to the use of compounds selected using a method consisting in:

bringing said compound into contact with the p38 protein, or a part or a homologue of this protein, or cells or fragments or lysates and, optionally, a suitable enzyme substrate, and measuring the binding of said compound to the p38 protein, for producing a medicinal product for the curative or preventive treatment of neurodegenerative diseases.

Definitions

For the purposes of the present invention, the name p38 protein covers the protein per se as described by Quevillon et al. (1999), and also all its homologous forms. The term "homologous forms" is intended to denote any proteins equivalent to the proteins under consideration, of diverse cellular origin and in particular derived from cells of human origin, or from other organisms, and having activity of the same type. Such homologous sequences may be obtained by hybridization experiments. For the purposes of the invention, it is sufficient for a sequence of this type to exhibit a significant percentage identity, in order to lead to a physiological behaviour which is similar to that of the p38 protein as claimed.

For the purposes of the present invention, the "percentage identity" between two nucleotide or amino acid sequences may be determined by comparing two sequences which are optimally aligned, through a window of comparison.

The part of the nucleotide or polypeptide sequence which is within the window of comparison may thus comprise additions or deletions (for example gaps) relative to the reference sequence (which does not comprise these additions or these deletions) so as to obtain optimal alignment of the two sequences.

The percentage is calculated by determining the number of positions at which an identical nucleic acid base or amino acid residue is observed for the two (nucleic acid or peptide) sequences compared, then dividing the number of positions at which there is identity between the two bases or amino acids residues by the total number of positions in the window of comparison, and then multiplying the result by 100 in order to obtain the percentage sequence identity.

The optimal alignment of the sequences for the comparison may be produced by computer, using known algorithms contained in the package from the company WISCONSIN GENETICS SOFTWARE PACKAGE, GENETICS COMPUTER GROUP (GCG), 575 Science Drive, Madison, WISCONSIN.

By way of illustration, the percentage sequence identity may be produced using the BLAST software (BLAST version 1.4.9 of March 1996, BLAST version 2.0.4 of February 1998 and BLAST version 2.0.6 of September 1998), using exclusively the default parameters (S. F. Altschul et al., J. Mol. Biol. 1990 215: 403–410, S. F. Altschul et al., Nucleic Acids Res. 1997 25: 3389–3402). Blast searches for sequences similar/homologous to a "request" reference sequence, using the algorithm of Altschul et al., mentioned above. The request sequence and the databases used may be peptide or nucleic acid sequences and databases, any combination being possible.

For the purposes of the present invention, the expression "high stringency hybridization conditions" will be intended to mean the following conditions:

1—Membrane competition and prehybridization:
Mix: 40 µl of salmon sperm DNA (10 mg/ml)+40 µl of human placenta DNA (10 mg/ml).
Denature for 5 min at 96° C., and then plunge the mixture into ice.
Add 2' SSC and pour 4 ml of formamide mix into the hybridization tube containing the membranes.
Add the mixture of the two denatured DNAs.
Incubate at 42° C. for 5 to 6 hours, with rotation.

2—Labelled probe competition:
Add to the labelled and purified probe 10 to 50 µl of Cot I DNA, depending on the amount of repetitions.
Denature for 7 to 10 min at 95° C.
Incubate at 65° C. for 2 to 5 hours.

3—Hybridization:
Remove the prehybridization mix.
Mix 40 µl of salmon sperm DNA+40 µl of human placental DNA; denature for 5 min at 96° C., and then plunge into ice.
Add 4 ml of formamide mix, the mixture of the two DNAs and the labelled probe/denatured Cot I DNA to the hybridization tube.
Incubate for 15 to 20 hours at 42° C., with rotation.

4—Washes:
One wash at ambient temperature in 2' SSC, to rinse.
Twice 5 minutes at ambient temperature, 2' SSC and 0.1% SDS at 65° C.
Twice 15 minutes at 65° C., 1' SSC and 0.1% SDS at 65° C.

5. Wrap the membranes in Saran wrap and expose.

The hybridization conditions described above are suitable for the hybridization under high stringency conditions of a nucleic acid molecule of length varying from 20 nucleotides to several hundred nucleotides. The hybridization conditions described above may be adjusted as a function of the length of the nucleic acid for which hybridization is sought or of the type of labeling chosen according to techniques known to those skilled in the art. Suitable hybridization conditions may, for example, be adjusted according to the teaching contained in the book by HAMES and HIGGINS (1985, "Nucleic acid hybridization: a practical approach", Hames and Higgins Ed., IRL Press, Oxford) or else in the book by F. AUSUBEL et al. (1989, Current Protocols in Molecular Biology, Green Publishing Associates and Wiley Interscience, N.Y.).

The proteins used in the methods according to the present invention may be obtained by any means known to those skilled in the art. They are, however, advantageously obtained by expressing the nucleic acids as described above, encoding these proteins, optionally inserted into expression vectors, in cells advantageously chosen, optionally followed by extraction and purification which may be complete or partial.

Advantageously, such a vector will comprise a nucleic acid chosen from the following nucleic acids:
a) a nucleic acid encoding a protein having at least 65% amino acid identity with a sequence SEQ ID NO:2 SEQ ID NO:5 or SEQ ID NO:8, or a peptide fragment or a variant of the latter;
b) a nucleic acid comprising a polynucleotide having at least 65% nucleotide identity with a nucleic acid having a sequence SEQ ID NO:1, SEQ ID NO:4 SEQ ID NO:7 or SEQ ID NO:10, or a fragment or a variant of the latter;
c) a nucleic acid hybridizing, under high stringency hybridization conditions, with a nucleic acid of sequence SEQ ID NO:1, SEQ ID NO:4, SEQ ID NO:7 or SEQ ID NO:10, or a fragment or a variant of the latter.

For the purposes of the present invention, the term "vector" will be intended to mean a circular or linear DNA or RNA molecule which is indifferently in single-stranded or double-stranded form.

According to one embodiment, the expression vector comprises a nucleic acid in accordance with the invention and regulatory sequences for directing the transcription and/or translation thereof.

According to an advantageous embodiment, a recombinant vector according to the invention comprises in particular the following elements:
(1) regulatory elements for expression of the nucleic acid to be inserted, such as promoters and enhancers;
(2) the coding sequence included in the nucleic acid in accordance with the invention to be inserted into such a vector, said coding sequence being placed in phase with the regulatory signals described in (1); and
(3) suitable transcription initiation and stop sequences.

In addition, the recombinant vectors used according to the invention may include one or more origins of replication in the cellular hosts in which their amplification or their expression is sought, labels or selectable markers.

By way of examples, the promoters for eukaryotic cells will comprise the thymidine kinase promoter of the HSV virus, the intermediate early promoter of the cytomegalovirus or else the mouse metallothionein promoter. In general, for the choice of a suitable promoter, those skilled in the art may advantageously refer to the book by SAMBROOK et al. (1989, "Molecular Cloning: A Laboratory Manual", 2nd ed., Cold Spring Harbor Laboratory Press, Cold Spring Harbor, N.Y.) or else to the techniques described by FULLER et al. (1996, Immunology in Current Protocols in Molecular Biology, Ausubel et al.)

The preferred vectors according to the invention are plasmids, such as, for example, the vectors pCDNA3 (Invitrogen), pQE70, pQE60, pQE9 (Qiagen), psiX174, pBluescript SA, pNH8A, pNH16A, pNH18A, pNH46A, pWL-NEO, pSV2CAT, pOG44, pXT1 or pSG (Stratagene). They may also be vectors of the baculovirus type, such as the vector pVL1392/1393 (Pharmingen) used to transfect cells of the Sf9 line (ATCC No. CRL 1711) derived from *Spodoptera frugiperda*. They may also be adenoviral vectors, such as the human adenovirus type 2 or 5. A recombinant vector according to the invention may also be a retroviral vector or an adeno-associated vector (AAV). Such adeno-associated vectors are, for example, described by FLOTTE et al. (1992, Am. J. Respir. Cell Mol. Biol., 7: 349–356).

Cells comprising a protein, a nucleic acid or a vector as described above, or fragments of these cells, or lysates of these cells, may be used to implement the present invention. The cellular hosts which can be used for producing the proteins of the invention by the recombinant pathway may be both eukaryotic and prokaryotic hosts. Among suitable eukaryotic hosts, mention may be made of animal cells, yeasts or fungi. In particular, as regards yeasts, mention may be made of yeasts of the *Saccharomyces, Kluyveromyces, Pichia, Schwanniomyces,* or *Hansenula* genus. As regards animal cells, mention may be made of COS, CHO, CI27, PC12, etc. cells. Among fungi, mention may be made more particularly of *Aspergillus* ssp. or *Trichoderma* ssp. As prokaryotic hosts, use is preferably made of the following bacteria: *E. coli, Bacillus* or *Streptomyces*. Thus, such lines are particularly advantageously the cell lines HEK 293, COS (ATCC No. CRL 1650), COS-M6, HeLa (ATCC No. CCL2), SH-SY5Y (ATCC No. CRL-2266), PC12 (ATCC No. CRL-1721), N2A (ATCC No. CCL-131) or else Cv 1 (ATCC No. CCL70), Sf-9 (ATCC No. CRL 1711), CHO (ATCC No. CCL-61) or 3T3 (ATCC No. CRL-6361).

Extracts of these cells may be prepared by any method known to those skilled in the art. Preferentially, they are prepared by mechanical grinding of the cells and then centrifugation of the suspensions obtained.

A subject of the present invention is also a method of curative or preventive treatment of neurodegenerative diseases, comprising the steps of:
  selecting said compound using a method consisting in:
    bringing said compound into contact with parkin and the p38 protein, or parts or homologues of these proteins, or cells or fragments or lysates and, optionally, a suitable enzyme substrate, and
    measuring the ability of said compound to modify the interaction between parkin and the p38 protein, and
  administering said compound to a patient suffering from said disease.

Finally, a subject of the invention is a method of curative or preventive treatment of neurodegenerative diseases, comprising the steps of:
  selecting said compound using a method consisting in:
    bringing said compound into contact with the p38 protein, or a part or a homologue of this protein, or cells or fragments or lysates and, optionally, a suitable enzyme substrate, and
    measuring the binding of said compound to the p38 protein,
  administering said compound to a patient suffering from said disease.

Such neurodegenerative diseases may be Parkinson's disease, or other chronic neurodegenerative diseases characterized by protein deposits in the brain, such as, for example: Huntingdon's disease or Alzheimer's disease.

Other subjects of the invention are compounds capable of modifying, at least partially, the interaction between the p38 protein and parkin, or parts or homologues of these proteins. Advantageously, such compounds slow down, inhibit or stimulate, at least partially, said interaction. Preferentially, these compounds are capable of binding the domain of interaction between the p38 protein, or a homologue thereof, and parkin, or to any other site on the p38 protein, or homologues, and having the effect of slowing down, inhibiting or stimulating, at least partially, said interaction. They may be of the peptide, nucleic acid, lipid or saccharide type or they may be antibodies.

The compounds of the invention may be formulated in pharmaceutical compositions for the purpose of topical, oral, parenteral, intranasal, intravenous, intramuscular, subcutaneous, intraocular, etc., administration. Preferentially, the pharmaceutical compositions contain vehicles which are pharmaceutically acceptable for an injectable formulation. They may in particular be isotonic, sterile, saline (monosodium phosphate, disodium phosphate, sodium chloride, potassium chloride, calcium chloride or magnesium chloride, etc., or mixtures of such salts) solutions, or dry compositions, in particular lyophilized compositions, which, by addition as appropriate of sterilized water or physiological saline, make it possible to constitute injectable solutes.

Preferentially, these compounds are peptides capable of interfering, at least partially, with the interaction of the p38 protein, or of one of its homologous forms, with parkin. This interference by a peptide according to the invention may manifest itself in various ways. The peptide claimed may slow down, inhibit or stimulate, at least partially, the interaction between the p38 protein, or one of its homologous forms, and parkin. According to a particular mode of the invention, the peptides are capable of binding to the domain of interaction between the p38 protein, or one of its homologous forms, and parkin, or to any other site on the p38 protein, or homologues, and having the effect of slowing down, inhibiting or stimulating, at least partially, said interaction.

More preferentially, the peptides of the invention comprise all or part of the peptide sequence encoding the p38 protein presented in SEQ ID NO:2 or one of its derivatives. For the purposes of the present invention, the term "derivative" denotes any sequence which differs from the sequence under consideration due to degeneracy of the genetic code, and which is obtained by one or more modifications of genetic and/or chemical nature, and also any sequence which hybridizes with these sequences, or fragments thereof, and which conserves the ability to interact at the level of the interaction between the p38 protein, or one of its homologues, and parkin. The expression "modification of genetic and/or chemical nature" may be understood to mean any mutation, substitution, deletion, addition and/or modification of one or more residues. The term "derivative" also comprises the sequences homologous to the sequence under consideration, which are derived from other cellular sources, and in particular from cells of human origin, or from other organisms, and having activity of the same type. Such homologous sequences may be obtained by hybridization experiments. The hybridizations may be carried out using nucleic acid libraries, using the native sequence or a fragment thereof as probe, under varying hybridization conditions (Maniatis et al., 1989).

Such derivatives may be generated for different purposes, such as in particular that of increasing their therapeutic effectiveness or of decreasing their side effects, or that of conferring on them novel pharmacokinetic and/or biological properties.

A peptide derived from the p38 protein and from the homologous forms mentioned may in particular be made of any peptide capable of interacting with parkin, but carrying an effector region which has been made nonfunctional. Such peptides may be obtained by deletion, mutation or disruption of this effector region on the p38 protein and homologous forms. Such modifications may be performed, for example, by in vitro mutagenesis, by introduction of additional elements or of synthetic sequences, or by deletions or substitutions of the original elements. When a derivative as defined above is produced, its activity of partial inhibitor of the attachment of the p38 protein, and of the homologous forms, to its site of attachment on parkin can be demonstrated. Any technique known to those skilled in the art may, of course, be used for this purpose.

There may also be fragments of the sequences indicated above, and in particular comprising at least 5, preferably at least 9, more preferentially at least 15, consecutive residues of the sequence SEQ ID NO:2. Such fragments may be generated in various ways. In particular, they may be synthesized by chemical process, on the basis of the sequences given in the present application, using peptide synthesizers known to those skilled in the art. They may also be synthesized via the genetic pathway, by expressing in a cellular host a nucleotide sequence encoding the desired peptide. In this case, the nucleotide sequence may be prepared chemically using an oligonucleotide synthesizer, on the basis of the peptide sequence given in the present application and of the genetic code. The nucleotide sequence may also be prepared from the sequences given in the present application, by enzymatic cleavage, ligation, cloning, etc., according to the techniques known to those skilled in the art, or by screening DNA libraries with probes developed from these sequences.

Moreover, the peptides of the invention may also be peptides which have a sequence corresponding to the site of interaction of the p38 protein, and of the homologous forms, on parkin.

Other peptides according to the invention are the peptides capable of competing, with the peptides defined above, for the interaction with their cellular target. Such peptides may be synthesized in particular on the basis of the sequence of the peptide under consideration, and their ability to compete with the peptides defined above may be determined.

Another subject of the invention lies in polyclonal or monoclonal antibodies or antibody fragments directed against a peptide as defined above. Such antibodies may be generated by methods known to those skilled in the art. In particular, these antibodies may be prepared by immunizing an animal against a peptide of the invention, taking blood, and isolating the antibodies. These antibodies may also be generated by preparing hybridomas according to the techniques known to those skilled in the art. More preferentially, the antibodies or antibody fragments of the invention have the ability to modify, at least partially, the interaction of the claimed peptides with parkin. Moreover, these antibodies may also be used to detect and/or assay the expression of p38 in biological samples and, consequently, to provide information regarding its state of activation.

The invention also relates to the compounds which are not peptide, or not exclusively peptide, in nature, which can be used as a pharmaceutical agent. It is in fact possible, based on the active protein motifs described in the present application, to produce molecules which modify the activity of p38, which are not exclusively peptide in nature, and which are compatible with pharmaceutical use.

A subject of the present invention is also any nucleotide sequence encoding a peptide according to the invention. It may in particular be a sequence comprising all or part of the sequence presented in SEQ ID NO:1, or one of its derivatives. For the purposes of the present invention, the term "derived sequence" is intended to mean any sequence which hybridizes with the sequence presented in SEQ ID NO:1, or with a fragment thereof, and which encodes a peptide according to the invention, and also the sequences resulting from these sequences by degeneracy of the genetic code. The various nucleotide sequences of the invention may be of artificial or non-artificial origin. They may be genomic, cDNA or RNA sequences, hybrid sequences or synthetic or semi-synthetic sequences. These sequences may be obtained either by screening DNA libraries (cDNA library, genomic DNA library), or by chemical synthesis, or by mixed methods including the chemical or enzymatic modification of sequences obtained by screening libraries, or by searching for homology in nucleic acid or protein databases.

Such nucleotide sequences may be used to produce the peptides of the invention. The present application thus relates to a method for preparing such a peptide, according to which a cell containing a nucleotide sequence according to the invention is cultured under conditions for expressing said sequence, and the peptide produced is recovered. In this case, the portion encoding said peptide is generally placed under the control of signals which allow its expression in a cellular host. The choice of these signals (promoters, terminators, secretion leader sequence, etc.) can vary as a function of the cellular host used. Moreover, the nucleotide sequences of the invention may be part of a vector which can replicate autonomously or which can integrate. More particularly, autonomously-replicating vectors may be prepared using sequences which replicate autonomously in the chosen host. As regards the integrating vectors, these may be prepared for example using sequences homologous to certain regions of the host's genome, which allow integration of the vector by homologous recombination. The conditions for obtaining these peptides may be those described above for the proteins used in the implementation of the methods which are the subjects of the present invention.

The nucleic acid sequences according to the invention may also be used to produce antisense oligonucleotides or genetic antisense, which can be used as pharmaceutical agents. Antisense sequences are short oligonucleotides which are complementary to the messenger RNA transcribed from a given gene, and consequently are capable of hybridizing specifically with it, inhibiting the translation thereof into protein. The nucleic acid sequences according to the invention may also be used to produce interference RNAs (iRNAs) or iRNAs which can be used as pharmaceutical agents. iRNAs are short double-stranded RNAs, one of the strands of which corresponds to the messenger RNA transcribed from a given gene, and consequently are capable of inhibiting the transcription thereof via a mechanism which is as yet poorly understood. A subject of the invention is thus the antisense or iRNA sequences capable of inhibiting, at least partially, the interaction of the p38 proteins on parkin. Such sequences may consist of all or part of the nucleic acid sequences defined above. They are generally sequences or fragments of sequences complementary to sequences encoding peptides which interact with parkin. Such oligonucleotides may be obtained by fragmentation or by chemical synthesis.

The sequences claimed may be used in the context of gene therapies, for transferring and expressing, in vivo, antisense sequences or peptides capable of modifying the interaction of the p38 protein with parkin. In this regard, the sequences may be incorporated into viral or nonviral vectors, allowing them to be administered in vivo (Kahn et al., 1991). As viral vectors in accordance with the invention, mention may be made most particularly of vectors of the adenovirus, retrovirus, adenovirus-associated virus (AAV) or herpesvirus type. A subject of the present application is also defective recombinant viruses comprising a heterologous nucleotide sequence encoding a polypeptide according to the invention.

The invention also makes it possible to produce nucleotide probes, which may or may not be synthetic, which are capable of hybridizing with the nucleotide sequences defined above, and which can be used in the context of a gene therapy. Such probes may be used in vitro as a diagnostic tool, for detecting the expression or overexpression of p38, or else for demonstrating genetic abnormalities (incorrect splicing, polymorphism, point mutations, etc.). These probes may also be used to demonstrate and isolate homologous nucleic acid sequences encoding peptides as defined above, from other cellular sources and preferentially from cells of human origin. The probes of the invention generally comprise at least 10 bases, and they may, for example, comprise up to all of one of the abovementioned sequences or of the strand complementary thereto. Preferentially, these probes are pre-labelled before they are used. For this, various techniques known to those skilled in the art may be used (radioactive or nonradioactive labeling, etc.).

A subject of the invention is also a pharmaceutical composition comprising as active principle at least one antibody and/or one antibody fragment or one nucleotide sequence as defined above.

Moreover, a subject of the invention is also the pharmaceutical compositions in which the peptides, antibodies, chemical molecules and nucleotide sequence defined above are combined with one another or with other active principles.

EXAMPLES

Other advantages of the present invention will become apparent on reading the examples which follow, which should be considered as non-limiting illustrations.

Example Materials and Techniques

1) Yeast Strain:

Strain L40 of the *S. cerevisiae* genus (Mata, his3D200, trp-1-901, leu2-3, 112, ade2, LYS2::(lexAop)4-HIS3, URA3::(lexAop)8-LacZ, GAL4, GAL80) was used to verify the protein-protein interactions when one of the protein partners is fused to the LexA protein. The latter is capable of recognizing the LexA response element which controls expression of the LacZ and His3 reporter genes.

It was cultured on the following culture media:
Complete YPD Medium:
Yeast extract (10 g/l) (Difco)
Bactopeptone (20 g/l) (Difco)
Glucose (20 g/l) (Merck)
This medium was solidified by adding 20 g/l of agar (Difco).
Minimum YNB Medium:
Yeast Nitrogen Base (without amino acids) (6.7 g/l) (Difco)
Glucose (20 g/l) (Merck)
This medium can be solidified by adding 20 g/l of agar (Difco). It can also be supplemented with amino acids and/or with 3-amino-1,2,4-triazole by adding CSM media [CSM-Leu, -Trp, -His (620 mg/l), CSM-Trp (740 mg/l) or CSM-Leu, -Trp (640 mg/l) (Bio101)] and/or 2.5 mM 3-amino-1,2,4-triazole.

2) Bacterial Strains:

*Escherichia coli* strain TG1, of genotype supE, hsd•5, thi, •(lac-proAB), F'[tra D36 pro A+B+laclq lacZ•M15], was used for the plasmid construction, as a means of amplifying and isolating recombinant plasmids used. It was cultured on the following medium:
LB Medium:
NaCl (5 g/l) (Prolabo)
Bactotryptone (10 g/l) (Difco)
Yeast extract (5 g/l) (Difco)
This medium is solidified by adding 15 µl of agar (Difco).
Ampicillin was used at 100 µg/ml; this antibiotic is used to select the bacteria which have received the plasmids carrying the gene for resistance to this antibiotic, as a marker.

*Escherichia coli* strain HB101, of genotype supE44, ara14, galK2, lacY1, •(gpt-proA)62, rpsL20(Strr), xy1-5, mt1-1, recA13, •(mcrC-mrr), HsdS☐(r☐m-) was used as a means for amplifying and isolating plasmids originating from the cDNA library originating from cells of the human Hela line.

It was cultured on
M9 medium: —Na2HPO4 (7 g/l) (Prolabo)
KH2PO4 (3 g/l) (Prolabo)
NH4Cl (1 g/l) (Prolabo)
NaCl (0.5 µl) (Prolabo)
Glucose (20 g/l) (Sigma)
MgSO4 (1 mM) (Prolabo)
Thiamine (0.001%) (Sigma)
This medium is solidified by adding 15 g/l of agar (Difco).
Leucine (50 mg/l) (Sigma) and proline (50 mg/l) (Sigma) must be added to the M9 medium to allow growth of the HB101 strain.

During the selection of plasmids originating from the two-hybrid cDNA library originating from cells of the HeLa line, leucine was not added to the medium since the plasmids carry a Leu2 selectable marker.

3) Plasmid:

The vector pLex9 (pBTM116) (Bartel et al., 1993) is a 5 kb vector homologous to pGBT10 which contains a multiple cloning site located downstream of the sequence encoding the bacterial repressor LexA and upstream of a terminator, to form a fusion protein.

pLex-HaRasVal12 is a pLex9 plasmid which contains the sequence encoding the HaRas protein mutated at position Val 12, known to interact with the mammalian Raf protein (Vojtek et al., 1993). This plasmid was used to test the specificity of interaction of the p38 protein in the L40 strain.

pLex-cAPP is a pLex9 plasmid which contains the sequence encoding the cytoplasmic domain of the APP protein, known to interact with the PTB2 domain of FE65. This plasmid was used to test the specificity of interaction of the p38 protein in the L40 strain.

4) Synthetic Oligonucleotides:

The following oligonucleotides may be used to obtain the PCR fragment corresponding to the central region of parkin bordered by the EcoRI and BamHI sites.

```
TTAAGAATTC GGAAGTCCAG CAGGTAG      (SEQ ID NO:11)

ATTAGGATCC CTACACACAA GGCAGGGAG    (SEQ ID NO:12)
```

The following oligonucleotides may be used to sequence the insert corresponding to the p38 gene.

```
GCGTTTGGAA TCACTACAG               (SEQ ID NO:13)

GGTCTCGGTG TGGCATC                 (SEQ ID NO:14)

CCGCTTGCTT GGAGGAAC                (SEQ ID NO:15)

CGTATTTCTC CGCCTTGG                (SEQ ID NO:16)

AATAGCTCGA GTCAGTGCAG GACAAGAG     (SEQ ID NO:17)
```

All oligonucleotides may be synthesized on the Applied System ABI 394-08 machine. They may be detached from the synthesis matrix with ammonia and precipitated twice with 10 volumes of n-butanol, then taken up in water. Quantification can be carried out by measuring optical density (1OD260 corresponds to 30 µg/ml).

5) Plasmid DNA Preparation

Plasmid DNA preparations, in small amounts and in large amounts, were carried out according to the protocols recommended by the manufacturer Quiagen of the DNA purification kits:
Quiaprep Spin Miniprep kit, ref: 27106
Quiaprep Plasmid Maxiprep kit, ref: 12163.

6) Enzymatic Amplification of DNA by PCR (Polymerase Chain Reaction):

The PCR reactions were carried out in a final volume of 100 µl in the presence of the DNA matrix, of dNTP (0.2 mM), of PCR buffer (10 mM Tris-HCl, pH 8.5, 1 mM MgCl2, 5 mM KCl, 0.01% gelatine), of 10–20 pmol of each of the oligonucleotides and of 2.5 IU of Ampli Taq DNA polymerase (Perkin Elmer). The mixture is covered with 2 drops of paraffin oil in order to limit evaporation of the sample. The machine used is the Appligene "Crocodile II".

A matrix denaturing temperature of 94° C., a hybridization temperature of 52° C. and an enzymatic elongation temperature of 72° C. may be used.

7) Ligations:

All the ligation reactions are carried out at 37° C. for one hour in a final volume of 20 µl in the presence of 100 to 200 ng of vector, 0.1 to 0.5 µg of insert, 40 IU of T4 DNA ligase enzyme (Biolabs) and a ligation buffer (50 mM Tris-HCl, pH 7.8; 10 mM MgCl2; 10 mM DTT; 1 mM ATP). The negative control consists of ligation of the vector in the absence of insert.

8) Transformation of the bacteria with a plasmid may be carried out according to the following protocol: 10 µL of the ligation volume is used to transform TG1 bacteria according to the method of Chung (Chung et al., 1989). After transformation, the bacteria are plated out onto an LB medium+ ampicillin and incubated for 16 h at 37° C.

9) DNA separation and extraction may be carried out as follows: The DNAs are separated as a function of their size by agarose gel electrophoresis according to Maniatis (Maniatis et al., 1989):

1% agarose gel (Gibco BRL) in a TBE buffer (90 mM Tris base; 90 mM borate; 2 mM EDTA)

10) Fluorescent Sequencing of Plasmid DNAs:

The sequencing technique used is derived from the method of Sanger (Sanger et al., 1977) and adapted for the sequencing by fluorescence developed by Applied Biosystems. The protocol used is that described by the designers of the system (Perkin Elmer, 1997).

11) Transformation of Yeast with a Plasmid:

The plasmids are introduced into yeast via a conventional technique of yeast transformation developed by Gietz (Gietz et al., 1992) and modified in the following way:

In the particular case of transformation of yeast with the cDNA library originating from cells of the HeLa line, the yeast used contains the plasmid pLex9-Parkin (135–290) encoding the central portion of parkin fused to the LexA protein. It is cultured in 200 ml of minimum YNB medium supplemented with amino acids CSM-Trp at 30° C. with shaking until a density of 107 cells/ml is obtained. To carry out the transformation of the yeasts according to the preceding protocol, we separated the cell suspension into 10 tubes of 50 ml, into which 5 µg of the library were added. The thermal shock was carried out for 20 minutes and the cells were then collected by centrifugation and resuspended in 100 ml of YPD medium for 1 h at 30° C. and in 100 ml of YNB medium supplemented with CSM □Leu, □Trp for 3 h 30 at 30° C. The transformation efficiency is determined by plating out various dilutions of transformed cells onto solid YNB medium supplemented with CSM-Trp, -Leu. After culturing for 3 days at 30° C., the colonies obtained were counted and the transformation rate per·µg of DNA of the cDNA library originating from cells of the Hela line was determined.

12) Isolation of Plasmids Extracted from Yeast:

5 ml of a yeast culture incubated for 16 h at 30° C. are centrifuged and taken up in 200 µl of a lysis buffer (1M sorbitol, 0.1M KH2PO4/K2HPO4, pH 7.4, 12.5 mg/ml zymolyase) and incubated for 1 h at 37° C. The lysate is then treated according to the protocol recommended by the manufacturer Quiagen of the DNA purification kit, Quiaprep Spin Miniprep kit, ref 27106.

13) b-galactosidase Activity Assay:

A sheet of nitrocellulose is pre-placed on the Petri dish containing the separated yeast clones. This sheet is then immersed in liquid nitrogen for 30 seconds in order to rupture the yeasts and thus to release the b-galactosidase activity. After thawing, the sheet of nitrocellulose is placed, colonies facing upwards, in another Petri dish containing a Whatman paper presoaked in 1.5 ml of PBS solution (60 mM Na2HPO4, 40 mM NaH2PO4, 10 mM KCl, 1 mM MgSO4, pH 7) containing 15 µl of X-Gal (5-bromo-4-chloro-3-indolyl-b-D-galactoside) containing 40 mg/ml of N,N-dimethylformamide. The dish is then placed in an incubator at 37° C. The assay is deemed positive when the colonies on the membrane turn blue after 12 hours.

14) Coimmunoprecipitation

The COS7 cells (106) were transfected with 6 µg of each plasmid, in the presence of DMRIE-C (Gibco), according to the protocol indicated by the supplier. After 48 h, the cells were harvested and lysed in the coimmunoprecipitation buffer (50 mM Tris-HCl, pH 8, 150 mM NaCl, 5% glycerol, 0.5% NP40, 0.2 mM Na3VO4 (Sigma), 4 mg/ml NaF (Sigma), protease inhibitors (Roche Diagnostics)). The supernatants obtained after centrifugation (4° C., 13 000 g, 30 min) were immunoprecipitated with anti-HA antibodies (clone 16B12, BabCO, 1–3 µg), as described (Elion, 1999). The immunoprecipitated proteins were separated on a denaturing polyacrylamide gel (SDS-PAGE, 10%) and analysed by Western blotting using anti-HA (BabCO, 1:1000) and anti-myc (clone 9E10, Santa Cruz, 1:400) antibodies.

15) Ubiquitinylation Experiments

The SH-SY5Y cells (3.5° 106) were transfected with the plasmids indicated (pcDNA3-myc-p38, 10 µg; pEGFP-N1, 10 µg; p6His-Ubiquitin, 5 µg; pcDNA3 up to 20 µg of total DNA), as described in the preceding paragraph. Forty-eight hours after transfection, the cells were treated with an inhibitor of proteasome activity (epoxymycin, Affiniti, 1 µM) for 8 h, and then lysed in the denaturing lysis buffer (6M guanidium-HCl, 0.1M Na2HPO4/NaH2PO4, 0.01M Tris-HCl, pH 8). The lysates, having been passed through a needle (18 G' 1.5 mm) 10 times, were centrifuged (4 000 g, 15 min, ambient T), and the supernatants were incubated in the presence of ProBond resin (Invitrogen, 50 µl) and imidazole (Sigma, 5 mM) with gentle shaking (3 h, ambient T). The ProBond resin was then washed (lysis buffer, once; 8M urea, 0.1M Na2HPO4/NaH2PO4, 0.01M Tris-HCl, pH 8, once; 8M urea, 0.[lacuna]M Na2HPO4/NaH2PO4, 0.01M Tris-HCl, pH 6.3 (buffer A)+0.2% Triton X-100 (Sigma), 3 times; buffer A+0.1% Triton X-100, once; buffer A+10 mM imidazole, once). The 6-His-ubiquitinylated proteins were eluted from the resin in the elution buffer (200 mM imidazole in 5% SDS, 0.15M Tris-HCl, pH 6.7, 30% glycerol, 0.72 [lacuna] b-mercaptoethanol), then separated on SDS-10% PAGE and analysed by anti-myc (clone 9E10, Santa Cruz, 1:400), anti-HA (BabCO, 1:1000) or anti-GFP (anti-GFP monoclonal, Boehringer Mannheim, 0.4 µg/ml) Western blotting.

16) Immunocytochemistry

The cells (COS7, 2.5' 104 and SH-SY5Y cells, 8' 104) were transfected with the plasmids indicated (pcDNA3-myc-p38, 0.5 ·g; or pcDNA3-myc-p38 and pcDNA3-HA-Parkin, 0.25 ·g of each), and treated or not treated with: epoxomicin (Affiniti, 1 µM), nocodazole (Sigma, 15 µg/ml), cytochalasin D (Sigma, 200 nM) overnight. Forty-eight hours after transfection, the cells were fixed and subjected to standard immunocytochemistry procedures. The polyclonal primary antibodies used were: anti-p38 (M. Mirande, 1:20 000), anti-Parkin (Asp5, 1:400), anti-proteasome 20S (Affiniti, 1:2500), anti-Hsp70 (Stressgen, 1:2500), anti-ubiquitin (Dako, 1:100) and anti-actin (Sigma, 1:100). The monoclonal primary antibodies were: anti -a-tubulin (clone DM 1A, Sigma, 1:1000), antivimentin (DAKO, clone V9, 1:100) and anti-myc (clone 9E10, Santa Cruz, 1:400). The secondary antibodies were: anti-mouse IgGs conjugated to the fluorochrome Alexa Fluor 488 (Interchim, 1:200) and anti-rabbit IgGs conjugated to the fluorochrome CY3 (Jackson ImmunoResearch, 1:500). The cells were analysed by confocal microscopy.

Example 1

Construction of a Vector for Expression of a Fusion Protein Produced from Fusion Between the Central Portion of Parkin and the Bacterial Repressor LexA Screening a library using the double-hybrid system requires the central region of parkin to be fused to a DNA-binding protein such as the bacterial repressor LexA. Expression of this fusion protein is produced using the vector pLex9 (cf. materials and methods), into which we have introduced, in the same reading frame as the sequence corresponding to the LexA protein, the sequence encoding the central region of parkin, which appears in the sequence presented in SEQ ID NO:8.

The 468 bp DNA fragment corresponding to the 156 amino acids of the central region of parkin, which begins at amino acid 135, was obtained by PCR using the oligonucleotides (SEQ ID NO:11 and No. 12) which also allowed us to introduce the EcoRI site at the 5' end and a stop codon and a BamHI site at the 3' end. The PCR fragment was introduced between the EcoRI and BamHI sites of the multiple cloning site of the plasmid pLex9, downstream of the sequence encoding the LexA protein, to give the vector pLex9-Parkin (135–290) (FIG. 1).

The construct was verified by DNA sequencing. This verification allowed us to show that this fragment does not exhibit mutations generated during the PCR reaction and that it is fused in the same open reading frame as that of the fragment corresponding to LexA.

Example 2

Screening the Fusion Library from Cells of the Hela Line

Screening a fusion library makes it possible to identify clones producing proteins fused to the transactivating domain of GAL4, which are able to interact with our protein of interest. This interaction makes it possible to reconstitute a transactivator which will then be capable of inducing expression of the His3 and LacZ reporter genes in the L40 strain.

To carry out this screening, we chose a fusion library produced from cDNA originating from cells of the HeLa line (Clontech).

Transformation of yeasts with the cDNA library originating from cells of the HeLa line and selection of positive clones During screening, it is necessary to maintain the probability that each independent plasmid of the fusion library is present in at least one yeast at the same time as the plasmid pLex9-Parkin (135–290). To maintain this probability, it is important to have a good efficiency of transformation of the yeast. For this, we chose a yeast transformation protocol giving an efficiency of 2.6' 105 transformed cells per µg of DNA. In addition, since cotransforming yeast with two different plasmids reduces this efficiency, we preferred to use a yeast pretransformed with the plasmid pLex9-Parkin (135–290). This L40 pLex9-Parkin (135–290) strain of phenotype His-, Lys-, Leu- was transformed with 50 µg of fusion library plasmid DNA. This amount of DNA enabled us to obtain, after estimation, 1.3' 107 transformed cells, which corresponds to a number which is slightly higher than the number of independent plasmids making up the library. According to this result, it may be considered that virtually all the plasmids of the library were used to transform the yeasts. The selection of the transformed cells capable of reconstituting a functional transactivator was done on a YNB medium supplemented with 2.5 mM 3-amino-1,2,4-triazole and 620 mg/l of CSM (Bio101) containing no histidine, no leucine and no tryptophan.

At the end of this selection, many clones with a His+ phenotype were obtained. A •b-galactosidase activity assay was carried out on these transformants in order to validate, through expression of the other reporter gene, LacZ, this number of clones obtained. 18 clones exhibited the His+, b-Gal+ double phenotype which may correspond to a protein-protein interaction.

Example 3

Isolation of the Library Plasmids from the Selected Clones

In order to identify the proteins which may interact with the central region of parkin, we extracted the fusion library plasmids contained in the yeasts selected during the double-hybrid screening. In order to be able to obtain a large amount thereof, this isolation requires prior transformation of E. coli with an extract of DNA from the positive yeast strains. Since the library plasmid contained in this extract is a yeast/E. coli shuttle plasmid, it may easily replicate in the bacterium. The library plasmid was selected by complementation of the HB101 bacterium, which is auxotrophic for leucine, on leucine-free medium.

The plasmid DNAs from the bacterial colonies obtained after transformation with yeast DNA extracts were analysed by digestion with restriction enzymes and separation of the DNA fragments on agarose gel. Among the 18 clones analysed, we obtained a clone containing a library plasmid having a profile different from the others. This plasmid, called pGAD-HeLa7, was studied more specifically.

Example 4

Determination of the Sequence of the Insert Contained in the Plasmid Identified

The insert contained in the plasmid identified was initially sequenced using the oligonucleotide (SEQ ID NO:13) complementary to the GAL4TA sequence close to the EcoRI site of insertion of the cDNA library originating from cells of the HeLa s line, and then, in a second step, using oligonucleotides (SEQ ID NO:14 to SEQ ID NO:17) corresponding to the sequence of the insert, obtained as the sequencing progressed.

Comparison of the sequence of this insert with the sequences contained in the GENBank and EMBL (European Molecular Biology Lab) databanks showed 100% homology, at the protein level, with the p38 protein. It is the product of the human gene JTV1, a structural component of aminoacyl-tRNA synthetase multiprotein complexes (Quevillon et al., 1999).

Example 5

Analysis of the Specificity of Interaction Between the Central Region of Parkin and the p38 Protein In order to determine the specificity of interaction between the fragment corresponding to the p38 protein and the central region of parkin, we carried out a two-hybrid test for specific interaction with other, non-relevant proteins. To carry out this test, we transformed the L40 strain with the control plasmids plex9-cAPP or pLex9-HaRasVal12 in place of the plasmid pLex9-Parkin (135–290), encoding, respectively, the cytoplasmic domain of APP or the HaRasVal12 protein, which are fused to the DNA-binding domain of LexA and with the plasmid isolated during the screening of the two-hybrid library. A b-Gal activity assay was carried out on the cells transformed with the various plasmids, in order to determine a protein-protein interaction. According to the result of the assay, only the yeasts transformed with the plasmid isolated during the screening of the two-hybrid library and with the plasmid pLex9-Parkin (135–290), exhibiting b-Gal+ activity, thus showing interaction between the central region of parkin and the p38 protein. This interaction proves to be specific since p38 does not appear to interact with the cAPP or HaRasVal12 proteins.

Example 6

Figure 2:
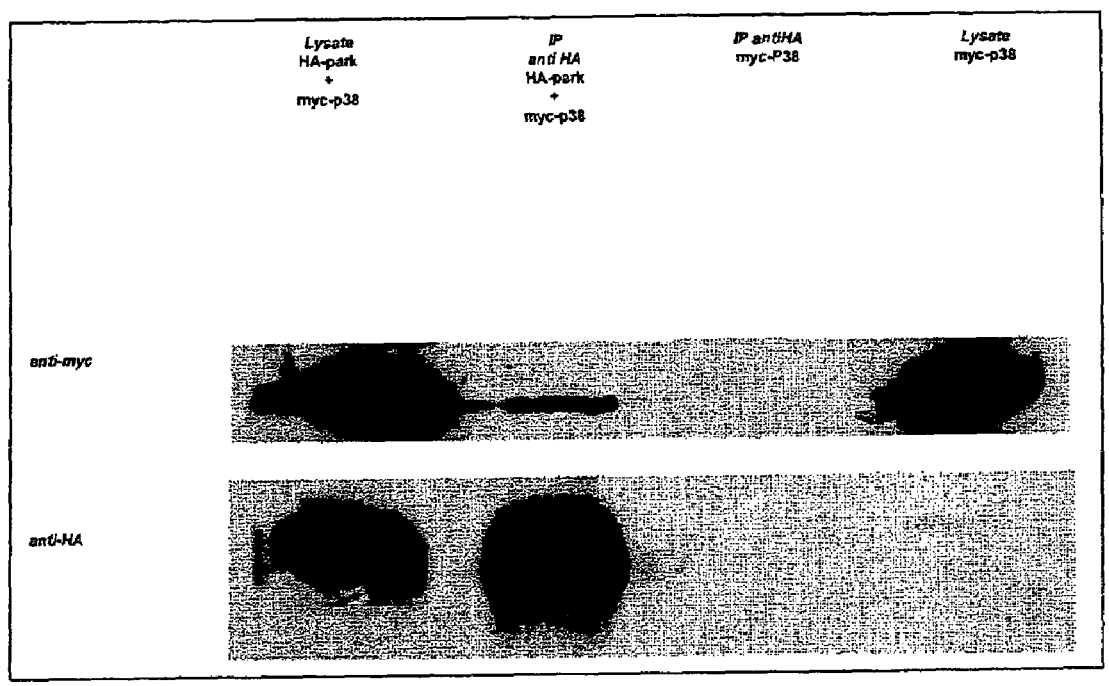
FIG. 2 is a photograph of a Western blot transfer illustrating the co-immunoprecipitation of Parkin and p38. The extracts were immunoprecipitated using antibodies directed against the HA epitope. Aliquots of the lysates and also the immunoprecipitated proteins were separated on a denaturing polyacrylamide gel (10%), and then analysed with anti-myc antibodies, in order to verify the co-immunoprecipitation of p38, or with anti-HA antibodies in order to confirm the immunoprecipitation of Parkin-HA-Ubi.

Confirmation of the Interaction Between Parkin and the p38 Protein by Coimmunoprecipitation In order to confirm the physical interaction between parkin and p38, coimmunoprecipitation experiments were carried out. Cells of the COS7 line were transiently transfected (1) with an expression plasmid directing expression of a p38 protein fused with an N-terminal myc (pcDNA3-myc-P38) epitope or (2) with pcDNA3-myc-P38, and also a second vector encoding a parkin variant deleted of its ubiquitin homology domain, fused with an N-terminal haemagglutinin epitope (pcDNA3-HA-Parkin-Ubi-, amino acids 77 to 465 of parkin). The cell extracts were then subjected to immunoprecipitation with a monocolonal antibody directed against the HA epitope, and the preciptates were then analysed by Western blotting using antibodies recognizing the myc epitope. When the two proteins were present in the lysate, coimmunoprecipitation of the p38 protein with the HA-Parkin-Ubi-protein could be demonstrated (FIG. 2).

Example 7

Subject of the Ubiquitinylation of the p38 Protein by Parkin

Figure 3:
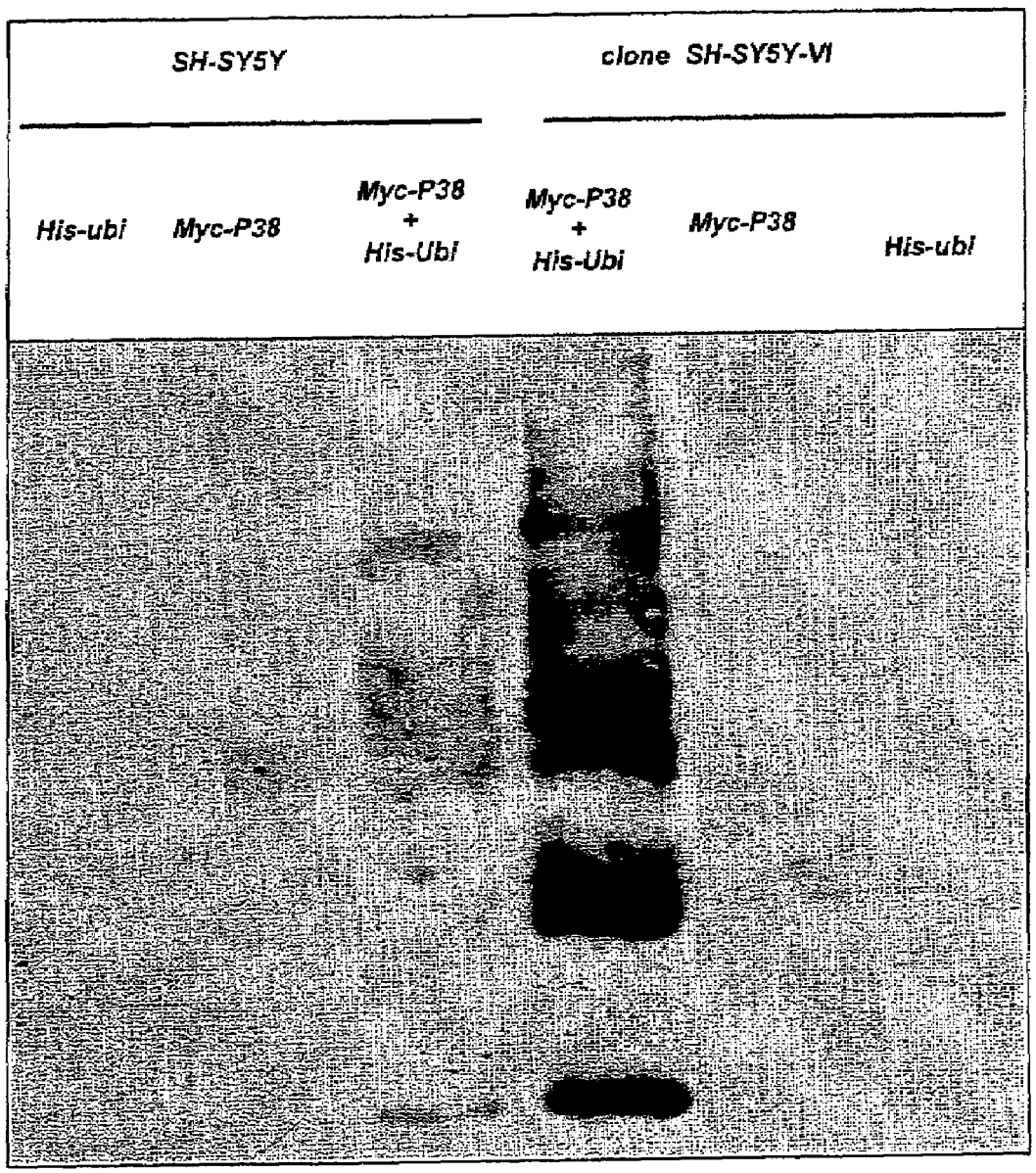
FIG. 3 is a photograph of a Western blot transfer illustrating the ubiquitinylation of the p38 protein by parkin. The cell proteins containing His epitopes were purified, separated on a denaturing polyacrylamide gel (10%) and analysed by Western blotting using anti-myc antibodies, in order to demonstrate the myc-P38 protein.
Figure 4G:
Figure 4H:
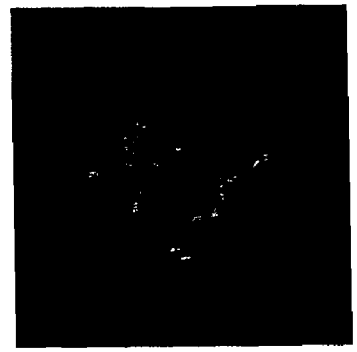
Figure 4I:
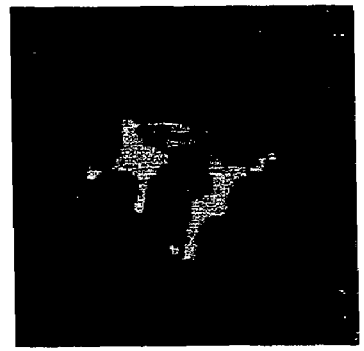
Figure 4J:
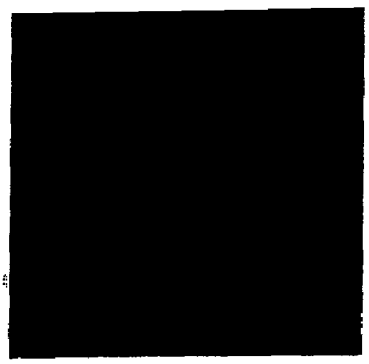
Figure 4K:
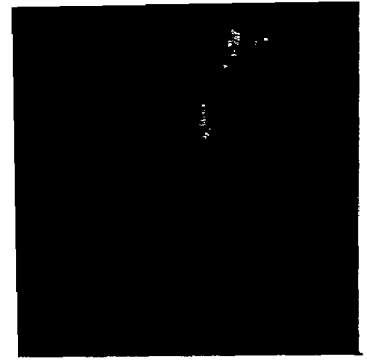
Figure 4L:
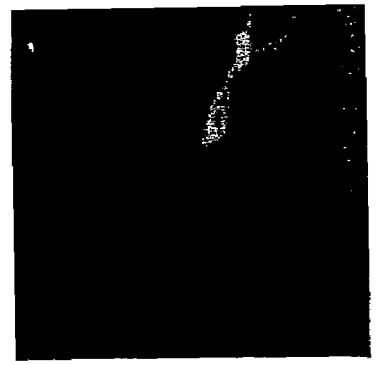

We studied the possibility that the p38 protein is a substrate for the E3 ubiquitin-protein ligase activity of Parkin. To do this, ubiquitinylation experiments were undertaken in a clone of the SH-SY5Y line stably overexpressing human parkin (SH-SY5Y-VI), which we had established previously in the laboratory. These cells, and also those of the unmodified SH-SY5Y line, were tranfected (1) with pcDNA3-myc-P38, (2) with a plasmid encoding ubiquintin in the form of a protein fused to a His epitope (pHis-Ubi), or (3) with pcDNA3-myc-P38 and p-His-Ubi concomitantly. After purification of the ubiquitinylated proteins using an Ni++-loaded affinity matrix, the ubiquitinylation of p38 was analysed by Western blotting using antibodies directed against the myc epitope. The p38 protein was found to be ubiquitinylated to a significantly greater degree in the SH-SY5Y-VI cells than in the unmodified cells of the SH-SY5Y line (FIG. 3). On the other hand, the control EGFP (enhanced green fluorescent protein) protein was not ubiquitinylated in either of the two lines (data not shown). These results indicate that p38 might be a substrate for parkin.

Example 8

Study of the Colocalization of Parkin and of the p38 Protein in Mammalian Cells

With the aim of providing additional elements to support there being a functional interaction between parkin and p38, we studied their intracellular localization after overexpression in cells of the COS7, SH-SY5Y and PC12 lines. The cells were cotransfected with the plasmid pcDNA3-myc-P38 and the vector pcDNA3-HA-Parkin or pcDNA3-HA-Parkin-Ubi. The parkin and p38 were demonstrated by immunofluorescence respectively with polyconal antibodies directed against a C-terminal epitope of human parkin (Asp5), and monoclonal antibodies recognizing the myc epitope of the myc-p38 fusion protein. The cells were then analysed by confocal microscopy. In the cells of the COS7 line, we observed an accumulation of the p38 protein in the perinuclear region. The parkin, which is a protein distributed homogeneously in the cytoplasm of cells when it is overexpressed alone, was systematically recruited into the perinuclear inclusions formed with p38 (FIG. 4). In the NGF-differentiated neuronal PC12 cells and SH-SY5Y cells, a similar homogeneous distribution of the two proteins was observed in the cytoplasm and the cell extensions (FIG. 4, G-I; J-L).

Example 9

Analysis of the Nature of the p38 Protein Perinuclear Cytoplasmic Inclusions

We analysed the nature and the composition of the p38 protein perinuclear inclusions formed when p38 is overexpressed in cells of the COS7 line. In particular, we wondered whether these inclusions could be of the aggresome type (Kopito et al., 2000). Using double-immunofluorescence and confocal microscopy techniques, we carried out a study of co-localization of the p38 protein inclusions with diverse endogenous aggresome markers. The p38 protein was found to colocalize with the 20 S proteasome, the HSP70 heat shock protein and, sometimes, ubiquitin. A redistribution of vimentin around the P38 protein inclusions was also observed. These data, and also the dispersion of the perinuclear aggregates by nocodazole, an agent which induces mircotubule depolymerization, demonstrate the "aggresome" nature of these aggregates. The formation of this type of inclusion had been described previously in the overexpression of proteins derived from disease genes (such as CFTR (cystic fibrosis conductance regulator), presenilin-1, or pathological forms of huntingtin (Kopito et al., 2000).

Example 10

Figure 5:
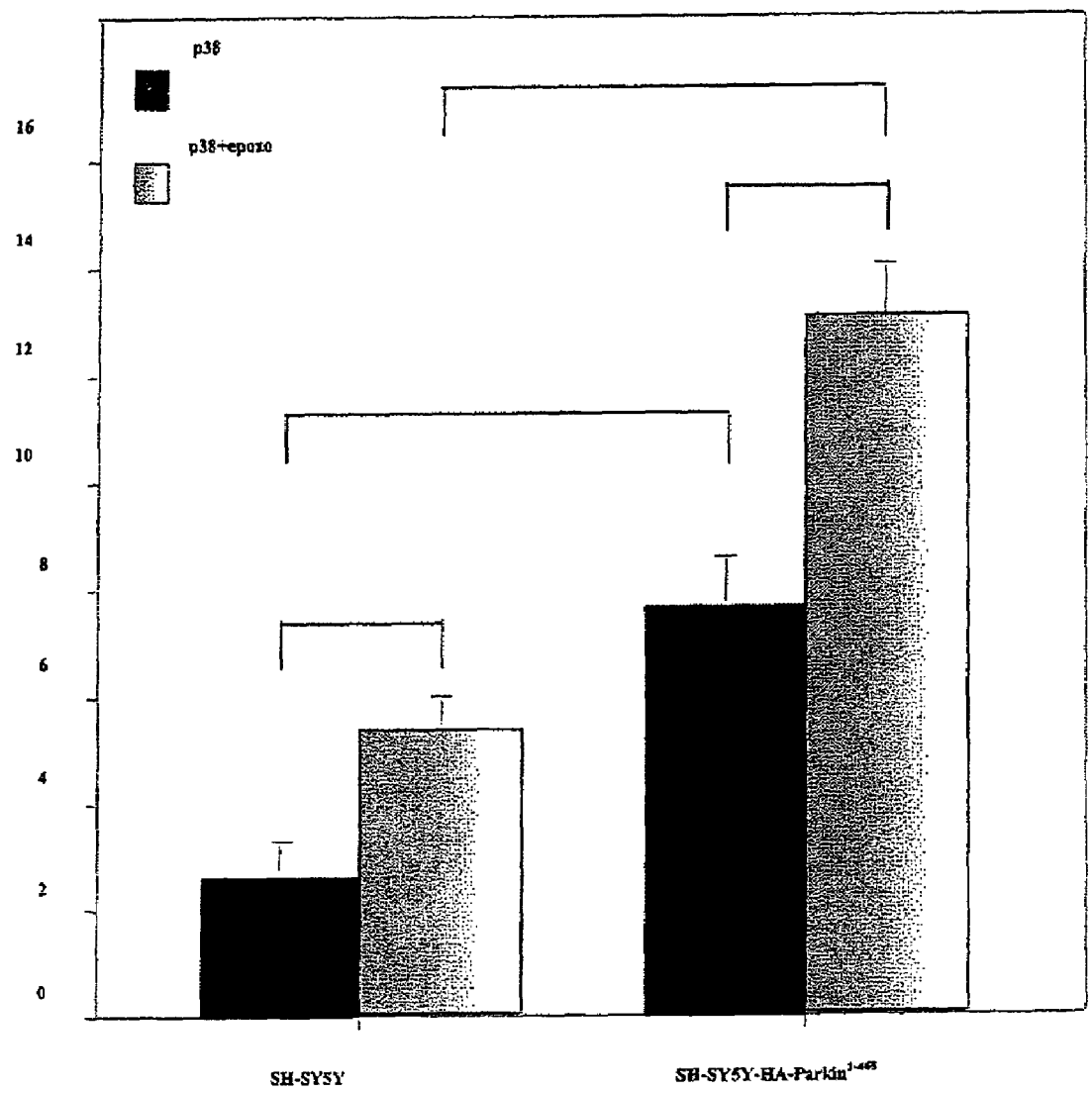
FIG. 5 illustrates, by immunofluorescence with anti-myc antibodies and anti-ubiquitin antibodies, the intracellular colocalization of the p38 aggregates with ubiquitin.

Study of the Effect of Parkin on the Formation of Cytoplasmic Inclusions Containing the p38 Protein The study of the functional interaction between parkin and the p38 protein was taken further in the cells of the SH-SY5Y line. The intracellular distribution of the p38 protein was studied after overexpression in SH-SY5Y or SH-SY5Y-VI cells. In the native cells, anti-p38 immunolabelling was distributed homogeneously in the cytoplasm as far as extensions. In approximatley 2.5% of transfected cells, juxtanuclear cytoplasmic inclusions were also observed. In the SH-SY5Y-VI line, the proportion of transfected cells exhibiting p38 aggregates was significantly higher (approximately 8%). These results suggest that ubiquitinylation of p38 by parkin precedes the formation of the inclusions. In the majority of cases, these aggregates were ubiquitinylated (FIG. 5). As observed previously in the cells of the COS7 line, the frequency and also the size of the p38-positive inclusions significantly increased when proteasome activity was inhibited with epoxomicin. No aggregation of the control EGFP protein was observed in either the cells of the native SH-SY5Y line or the SH-SY5Y-VI cells.

Example 11

Screening Assay in Yeast

The *Saccharomyces cerevisiae* strain used for the screening can be the L40 strain used to clone the p38 protein. However, this strain must contain the URA3 reporter gene in place of the HIS3 reporter gene under the control of a promoter containing a sequence to which the LexA protein attaches to induce transcription. This strain may also contain a disruption in the erg6 gene and/or genes such as pdr5 or pdr11, to increase cell permeability to the compounds tested during the screening (WO96/10082).

This strain is simultaneously transformed with the two plasmids encoding the p38 protein or parkin used in the previous two-hybrid test or else encoding homologous or truncated forms of these two proteins. The interaction between these proteins confers a Ura+phenotype on the doubly-transformed strain, by reconstituting a transcription factor capable of inducing transcription of the URA3 reporter gene. This Ura+ phenotype also makes it possible to use the sensitivity of the strain to 5-fluoorotic acid (5FOA) for reverse two-hybrid "positive" screening. The term "positive" screening is intended to mean the selection of inhibitors of the interaction Parkin-p38 or equivalent which induces restoration of yeast growth on a medium containing 5-fluoroorotic acid.

Example of Screening Assay:

The strain used to screen for inhibitors of the interaction Parkin-p38 or equivalent can be conserved at −80° C. in the form of frozen suspensions containing about 2' 107 cfu/ml in a medium containing 15% glycerol.

1 ml of these frozen suspensions can be used to seed a 500 ml Erlenmeyer flask containing 150 ml of medium containing 20 g/l glucose, 6.7 g/l YNB (yeast nitrogen base, Difco) and 0.64 g/l CSM without leucine and without tryptophan (complete supplement mixture, Bio101), and incubated at 30° C. for 24 hours.

This culture can be diluted in a sterile solution of 6.7 g/l YMB so as to obtain an optical density at 600 nm of about 0.07 OD.

This suspension will be used to seed 120×120 mm Petri dishes filled with 38 ml of agar-agar medium containing 20 g/l glucose, 6.7 g/l YNB, 0.64 g/l CSM without leucine and without tryptophan, 0.35 g/l 5FOA (Sigma ref. F5013) and 20 g/l agar. The medium is sterilized for 15 minutes at 121° C.; the YBN, the glucose and the 5FOA are added after sterilization, in the form of concentrated solutions, to the medium kept at 60° C.

The dishes may be seeded with the yeast strain by flooding them with 15 ml of yeast suspension per dish. The excess is immediately removed by drawing it off, and the dishes will be dried open under PSM for 20 min.

The compounds are deposited from 10 mM solutions in pure DMSO, distributed in 96-well or 384-well microplates. The undiluted 10 mM solutions are deposited, in the form of drops, at the surface of the dishes by pipette with disposable tips, or alternatively by replication using a needle replicator which, after each use, is rinsed in a bath of alcohol and/or DMSO, and then dried by contact with absorbent paper and/or passage under a stream of sterile air.

A solution at 0.2 mg/ml in water, conserved at 4° C., can optionally be deposited as a control.

The dishes are then incubated at 30° C. for 48 h and/or 72 h and they may be read by visual examination. The deposits which have given a halo or a ring of strain growth which is distinct from the strain growth in the presence of 5FOA are pinpointed. The control 6-azauridine which restores strain growth in this assay may be used as an internal control for the assay. The compounds which have made it possible to obtain such a response of strain growth restoration are identified as being positive and recorded in a database.

An assay for confirmation of the positive compounds, and/or for specificity by comparing several strains containing genes encoding different proteins, may be carried out according to the same basic protocol.

Example 12

Screening Assay by Measuring the Parkin-P38 Interaction by Homogeneous Time Resolved Fluorescence ("HTRF")

The assay measures the interaction between parkin and p38 in homogeneous phase using the Homogeneous Time Resolved Fluorescence ("HTRF") technology described by Mathis (1995 and 1999). The format described below is an example of indirect and generic format which may be used to screen for molecules which interfere with this interaction.

Figure 6B:
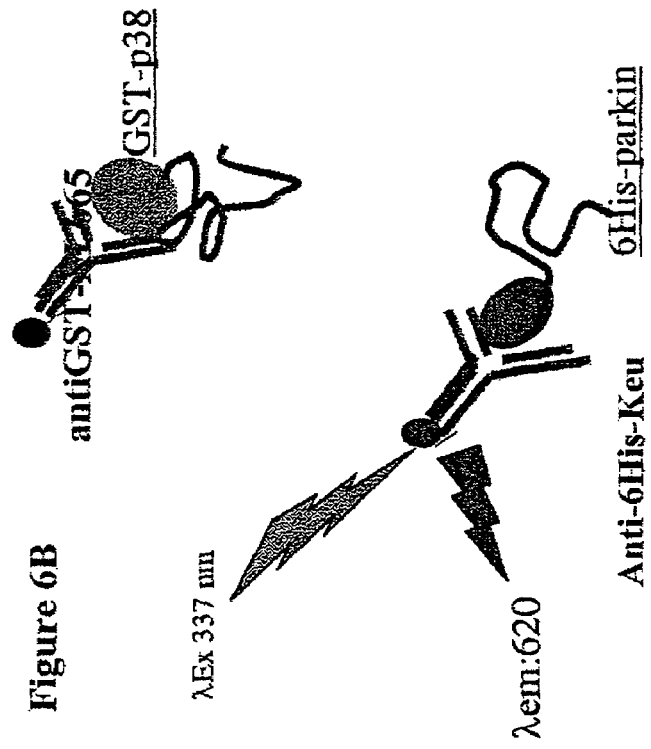
FIGS. 6A and 6B represent diagrammatically the principle of HTRF (Homogeneous Time Resolved Fluorescence) technology.
Figure 6A:
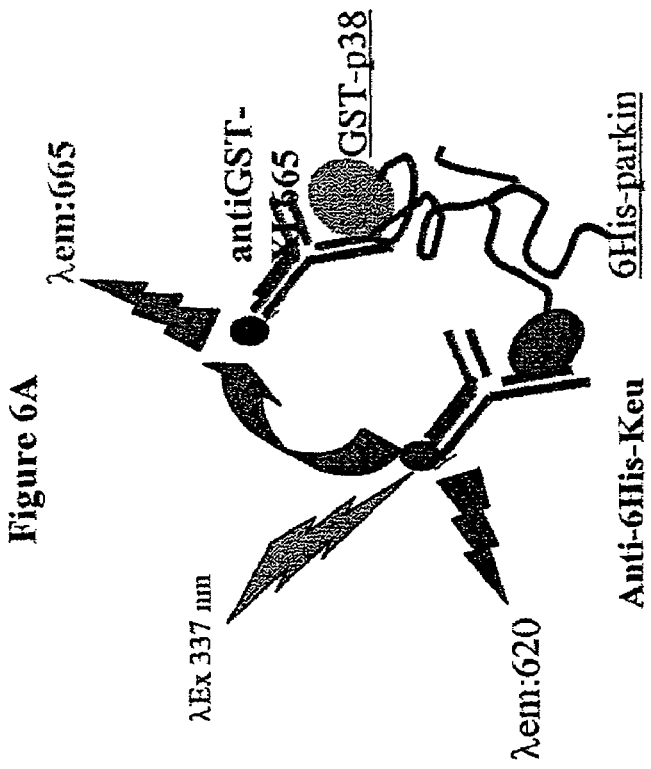

As represented diagrammatically in FIGS. 6A and 6B, the parkin protein of sequence SEQ ID NO:8 is fused with an N-terminal tag, such as polyhistidine (6His).

The p38 protein having the sequence SEQ ID NO:2 is fused with an N-terminal tag such as, for example, a residue of 33 amino acids of the Glutathione S transferase (GST) protein.

These two proteins are incubated in a suitable reaction buffer.

After a period of incubation, the HTRF reagents are added, namely: anti-polyhistidine antibodies labelled with europium cryptate (anti-6His-Keu) which recognize the His-parkin protein and anti-GST antibodies labelled with allophycocyanin (anti-GST-XL665) which recognize the GST-p38 protein.

When the parkin/p38 interaction occurs, (FIG. 6A), and only in the case of interaction, the europium cryptate is in the proximity of XL665. A transfer of energy between the europium cryptate and the XL665 occurs after excitation at 337 nm, generating a signal recorded at 665 nm (lem 665). The fluorescence emitted at 620 nm by the europium cryptate excited at 337 nm is also recorded (lem 620).

The HTRF signal is expressed in the form of an em665/em620 ratio. The value of this ratio depends only on the concentration of parkin-p38 complex, and virtually no account is taken of the possible fluorescence of the reaction medium.

Finally, the signal is expressed in DeltaF according to the following formula: If "Maxi" corresponds to the wells in which the interaction takes place (3% DMSO, his Parkin, gst-p38), and "Mini" corresponds to the wells which mimic the reaction of interaction inhibition (i.e. well without one of the 2 partners), the degree of interaction is given as Delta F=(ratioMaxi−ratiomini)/ratioMaxi.

Materials and Methods
Multiwell plates: 384- or 96-half-well, black
Detector: Discovery™ (Packard) or Rubystar™ (BMG)
Proteins:
  6His-Parkin: can be expressed in *Kluveromyces lactis*. In a standard manner, the cells are cultured on lactose, centrifuged, lysed and passed over a nickel chelate column according to the supplier's recommendations, in order to purify this protein: storage buffer: 50 mM Tris pH 7, 10% glycerol, 1 mM DTT, 100 mM NaCl.
  Untagged parkin: the 6His-parkin protein is expressed and purified as described above. A sequence recognized by proteases was inserted between the N-terminal polyhistidine tag and the sequence encoding parkin. Thus, the tag can be cleaved using a protease, for example, thrombin, according to the supplier's recommendations.
  GST-p38 can be expressed in *E. coli*, with, for example, the BL21 strain. In a standard manner, the cells are induced with 2 mM IPTG for 4 h at 37° C., centrifuged and lysed with glass beads. After being passed over a glutathione-sepharose 4B column, according to the supplier's recommendations, the protein is harvested with a purity of approximately 70–80%.

Possible storage buffer: 50 mM Tris pH 7, 20% glycerol, 1 mM DTT.

Buffers

Standard reaction buffer: 10 mM Hepes pH 7; 0.01% Tween 20

HTRF buffer: 50 mM Hepes pH 7, 100 mM KF, 1 g/l BSA.

HTRF reagents: anti-His-Cryptate and anti-GST-XL665 marketed by Cis bio international.

The assay protocol consists in adding, to the wells of a 96-half-well or 384-well plate, the reagents according to the protocol described in the table below:

Name of the reagent Maxi mini sample
3% DMSO diluted in the reaction buffer  10 ml 0  0
Molecule at 10 mM diluted in the reaction buffer (3% DMSO final concentration) 0 0  10 ml
Parkin (1 to 10 μM) (example at 3 mM) diluted in the reaction buffer with 3% DMSO (Reference inhibitor) 0  10 ml
6His-parkin (10 to 1000 nM) (example: 300nM) diluted in reaction buffer (i.e. final concentration of 100 nM, for example)  10 ml
GST-p38 (10 to 1000 nP) (example: 360 nM) diluted in reaction buffer (i.e. final concentration of 120 nM, for example)  10 ml
Incubate for 10 min at ambient temperature
Anti-6His-Keu- (10 to 50 ng/30 ml reaction) (example: 20 ng/30·ml) diluted in HTRF buffer Anti-GST-XL665 (100 to 1000 ng/30 ml reaction) (example: 30 ng··ml) diluted in HTRF buffer 30 ml
Read after 40 min of incubation at ambient temperature
"Maxi": corresponds to the wells in which the interaction takes place (3% DMSO, His Parkin, GST-p38),
"Mini": corresponds to the wells which mimic the reaction of interaction inhibition (i.e. well without one of the 2 partners),
"Sample": corresponds to the wells in which the interaction takes place in the presence of a molecule to be tested (his Parkin, gst-p38, molecule),

What is claimed is:

1. A method for screening a candidate compound for effectiveness in modifying the interaction between a p38 protein and a parkin protein comprising the steps of:
  a) exposing a sample comprising said p38 protein and parkin protein to said candidate compound; and
  b) measuring the interaction between said p38 protein to said parkin protein and comparing it to a control sample comprising said p38 protein and parkan protein without said candidate compound.

2. The method of claim 1 wherein said sample further comprises an enzyme substrate.

3. The method of claim 1, wherein said method is performed in vitro.

4. The method of claim 3, wherein said p38 protein is expressed in yeast.

5. The method of claim 1, wherein said p38 protein is selected from the group consisting of:
  a) a polypeptide encoded by the polynucleotide of SEQ ID NO:1,
  b) a polypeptide comprising the amino acid sequence of SEQ ID NO:2,
  c) a polypeptide encoded by the polynucleotide of SEQ ID NO:4,
  d) a polypeptide having at least 65% identity to a polypeptide encoded by the polynucleotide of SEQ ID NO:1,
  e) a polypeptide having at least 65% identity to a polypeptide comprising the amino acid sequence of SEQ ID NO:2, and
  f) a polypeptide having at least 65% identity to a polypeptide encoded by the polynucleotide of SEQ ID NO:4.

6. The method of claim 1, wherein said parkin is selected from the group consisting of:
  a) a polypeptide encoded by the polynucleotide of SEQ ID NO:7,
  b) a polypeptide comprising the amino acid sequence of SEQ ID NO:8,
  c) a polypeptide encoded by the polynucleotide of SEQ ID NO:10,
  d) a polypeptide having at least 65% identity to a polypeptide encoded by the polynucleotide of SEQ ID NO:7,
  e) a polypeptide having at least 65% identity to a polypeptide comprising the amino acid sequence of SEQ ID NO:8,
  f) a polypeptide having at least 65% identity to a polypeptide encoded by the polynucleotide of SEQ ID NO:10.

* * * * *

SEQUENCE LISTING

<160> NUMBER OF SEQ ID NOS: 22

<210> SEQ ID NO 1
<211> LENGTH: 1131
<212> TYPE: DNA
<213> ORGANISM: Homo sapiens
<220> FEATURE:
<221> NAME/KEY: CDS
<222> LOCATION: (1)..(963)

<400> SEQUENCE: 1

```
atg ccg atg tac cag gta aag ccc tat cac ggg ggc ggc gcg cct ctc        48
Met Pro Met Tyr Gln Val Lys Pro Tyr His Gly Gly Gly Ala Pro Leu
1               5                   10                  15 cgt gtg gag ctt ccc acc tgc atg tac cgg ctc ccc aac gtg cac ggc        96
Arg Val Glu Leu Pro Thr Cys Met Tyr Arg Leu Pro Asn Val His Gly
            20                  25                  30 agg agc tac ggc cca gcg ccg ggc gct ggc cac gtg cag gaa gag tct       144
Arg Ser Tyr Gly Pro Ala Pro Gly Ala Gly His Val Gln Glu Glu Ser
        35                  40                  45 aac ctg tct ctg caa gct ctt gag tcc cgc caa gat gat att tta aaa       192
```

```
                Asn Leu Ser Leu Gln Ala Leu Glu Ser Arg Gln Asp Asp Ile Leu Lys
                 50                  55                  60 cgt ctg tat gag ttg aaa gct gca gtt gat ggc ctc tcc aag atg att          240
Arg Leu Tyr Glu Leu Lys Ala Ala Val Asp Gly Leu Ser Lys Met Ile
 65                  70                  75                  80 caa aca cca gat gca gac ttg gat gta acc aac ata atc caa gcg gat          288
Gln Thr Pro Asp Ala Asp Leu Asp Val Thr Asn Ile Ile Gln Ala Asp
                 85                  90                  95 gag ccc acg act tta acc acc aat gcg ctg gac ttg aat tca gtg ctt          336
Glu Pro Thr Thr Leu Thr Thr Asn Ala Leu Asp Leu Asn Ser Val Leu
                100                 105                 110 ggg aag gat tac ggg gcg ctg aaa gac atc gtg atc aac gca aac ccg          384
Gly Lys Asp Tyr Gly Ala Leu Lys Asp Ile Val Ile Asn Ala Asn Pro
                115                 120                 125 gcc tcc cct ccc ctc tcc ctg ctt gtg ctg cac agg ctg ctc tgt gag          432
Ala Ser Pro Pro Leu Ser Leu Leu Val Leu His Arg Leu Leu Cys Glu
130                 135                 140 cac ttc agg gtc ctg tcc acg gtg cac acg cac tcc tcg gtc aag agc          480
His Phe Arg Val Leu Ser Thr Val His Thr His Ser Ser Val Lys Ser
145                 150                 155                 160 gtg cct gaa aac ctt ctc aag tgc ttt gga gaa cag aat aaa aaa cag          528
Val Pro Glu Asn Leu Leu Lys Cys Phe Gly Glu Gln Asn Lys Lys Gln
                165                 170                 175 ccc cgc caa gac tat cag ctg gga ttc act tta att tgg aag aat gtg          576
Pro Arg Gln Asp Tyr Gln Leu Gly Phe Thr Leu Ile Trp Lys Asn Val
                180                 185                 190 ccg aag acg cag atg aaa ttc agc atc cag acg atg tgc ccc atc gaa          624
Pro Lys Thr Gln Met Lys Phe Ser Ile Gln Thr Met Cys Pro Ile Glu
                195                 200                 205 ggc gaa ggg aac att gca cgt ttc ttg ttc tct ctg ttt ggc cag aag          672
Gly Glu Gly Asn Ile Ala Arg Phe Leu Phe Ser Leu Phe Gly Gln Lys
210                 215                 220 cat aat gct gtc aac gca acc ctt ata gat agc tgg gta gat att gcg          720
His Asn Ala Val Asn Ala Thr Leu Ile Asp Ser Trp Val Asp Ile Ala
225                 230                 235                 240 att ttt cag tta aaa gag gga agc agt aaa gaa aaa gcc gct gtt ttc          768
Ile Phe Gln Leu Lys Glu Gly Ser Ser Lys Glu Lys Ala Ala Val Phe
                245                 250                 255 cgc tcc atg aac tct gct ctt ggg aag agc cct tgg ctc gct ggg aat          816
Arg Ser Met Asn Ser Ala Leu Gly Lys Ser Pro Trp Leu Ala Gly Asn
                260                 265                 270 gaa ctc acc gta gca gac gtg gtg ctg tgg tct gta ctc cag cag atc          864
Glu Leu Thr Val Ala Asp Val Val Leu Trp Ser Val Leu Gln Gln Ile
                275                 280                 285 gga ggc tgc agt gtg aca gtg cca gcc aat gtg cag agg tgg atg agg          912
Gly Gly Cys Ser Val Thr Val Pro Ala Asn Val Gln Arg Trp Met Arg
                290                 295                 300 tct tgt gaa aac ctg gct cct ttt aac acg gcc ctc aag ctc ctt aag          960
Ser Cys Glu Asn Leu Ala Pro Phe Asn Thr Ala Leu Lys Leu Leu Lys
305                 310                 315                 320 tga attgccgtaa ctgattttaa agggtttaga ttttaagaat ggtgctcttt             1013
catgcctatt atcagtaagg ggacttgtat tagagtcaga gtcttttat ttaggccagt       1073 tgtcaagtgt caataaaagc atcatgtaat ttaaaaaaaa aaaaaaaaa aactcgag         1131

<210> SEQ ID NO 2
<211> LENGTH: 320
<212> TYPE: PRT
<213> ORGANISM: Homo sapiens
```

-continued

```
<400> SEQUENCE: 2

Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Glu Glu Ser
        35                  40                  45

Asn Leu Ser Leu Gln Ala Leu Glu Ser Arg Gln Asp Asp Ile Leu Lys
    50                  55                  60

Arg Leu Tyr Glu Leu Lys Ala Ala Val Asp Gly Leu Ser Lys Met Ile
65                  70                  75                  80

Gln Thr Pro Asp Ala Asp Leu Asp Val Thr Asn Ile Ile Gln Ala Asp
                85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
130                 135                 140

His Phe Arg Val Leu Ser Thr Val His Thr His Ser Ser Val Lys Ser
145                 150                 155                 160

Val Pro Glu Asn Leu Leu Lys Cys Phe Gly Glu Asn Lys Lys Gln
                165                 170                 175

Pro Arg Gln Asp Tyr Gln Leu Gly Phe Thr Leu Ile Trp Lys Asn Val
                180                 185                 190

Pro Lys Thr Gln Met Lys Phe Ser Ile Gln Thr Met Cys Pro Ile Glu
            195                 200                 205

Gly Glu Gly Asn Ile Ala Arg Phe Leu Phe Ser Leu Phe Gly Gln Lys
        210                 215                 220

His Asn Ala Val Asn Ala Thr Leu Ile Asp Ser Trp Val Asp Ile Ala
225                 230                 235                 240

Ile Phe Gln Leu Lys Glu Gly Ser Ser Lys Glu Lys Ala Ala Val Phe
                245                 250                 255

Arg Ser Met Asn Ser Ala Leu Gly Lys Ser Pro Trp Leu Ala Gly Asn
                260                 265                 270

Glu Leu Thr Val Ala Asp Val Val Leu Trp Ser Val Leu Gln Gln Ile
            275                 280                 285

Gly Gly Cys Ser Val Thr Val Pro Ala Asn Val Gln Arg Trp Met Arg
        290                 295                 300

Ser Cys Glu Asn Leu Ala Pro Phe Asn Thr Ala Leu Lys Leu Leu Lys
305                 310                 315                 320

<210> SEQ ID NO 3
<211> LENGTH: 320
<212> TYPE: PRT
<213> ORGANISM: Homo sapiens

<400> SEQUENCE: 3

Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Glu Glu Ser
        35                  40                  45
```

```
Asn Leu Ser Leu Gln Ala Leu Glu Ser Arg Gln Asp Asp Ile Leu Lys
     50                  55                  60

Arg Leu Tyr Glu Leu Lys Ala Ala Val Asp Gly Leu Ser Lys Met Ile
 65                  70                  75                  80

Gln Thr Pro Asp Ala Asp Leu Asp Val Thr Asn Ile Ile Gln Ala Asp
                 85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
    130                 135                 140

His Phe Arg Val Leu Ser Thr Val His Thr His Ser Ser Val Lys Ser
145                 150                 155                 160

Val Pro Glu Asn Leu Leu Lys Cys Phe Gly Glu Gln Asn Lys Lys Gln
                165                 170                 175

Pro Arg Gln Asp Tyr Gln Leu Gly Phe Thr Leu Ile Trp Lys Asn Val
            180                 185                 190

Pro Lys Thr Gln Met Lys Phe Ser Ile Gln Thr Met Cys Pro Ile Glu
        195                 200                 205

Gly Glu Gly Asn Ile Ala Arg Phe Leu Phe Ser Leu Phe Gly Gln Lys
    210                 215                 220

His Asn Ala Val Asn Ala Thr Leu Ile Asp Ser Trp Val Asp Ile Ala
225                 230                 235                 240

Ile Phe Gln Leu Lys Glu Gly Ser Ser Lys Glu Lys Ala Ala Val Phe
                245                 250                 255

Arg Ser Met Asn Ser Ala Leu Gly Lys Ser Pro Trp Leu Ala Gly Asn
            260                 265                 270

Glu Leu Thr Val Ala Asp Val Val Leu Trp Ser Val Leu Gln Gln Ile
        275                 280                 285

Gly Gly Cys Ser Val Thr Val Pro Ala Asn Val Gln Arg Trp Met Arg
    290                 295                 300

Ser Cys Glu Asn Leu Ala Pro Phe Asn Thr Ala Leu Lys Leu Leu Lys
305                 310                 315                 320

<210> SEQ ID NO 4
<211> LENGTH: 1233
<212> TYPE: DNA
<213> ORGANISM: Mus musculus
<220> FEATURE:
<221> NAME/KEY: CDS
<222> LOCATION: (78)..(1040)

<400> SEQUENCE: 4
ggctgctgtc tgaggtggcc ttgggtggct tctgagcgtt cctgtccctc gcccgctacc      60
ttccttgggt tcccacc atg ccg atg tac cag gta aag ccc tat cat gga        110
                   Met Pro Met Tyr Gln Val Lys Pro Tyr His Gly
                     1               5                  10 ggc agc gca cct ctg cgt gta gag ctt cca acc tgc atg tac cgg ctc       158
Gly Ser Ala Pro Leu Arg Val Glu Leu Pro Thr Cys Met Tyr Arg Leu
             15                  20                  25 ccc aac gtg cac agc aag acc acc agc ccc gcc acc gac gcg ggc cac       206
Pro Asn Val His Ser Lys Thr Thr Ser Pro Ala Thr Asp Ala Gly His
         30                  35                  40 gtg cag gaa aca tcc gag cct tct ttg caa gcc ctt gaa tct cgc caa       254
Val Gln Glu Thr Ser Glu Pro Ser Leu Gln Ala Leu Glu Ser Arg Gln
     45                  50                  55
```

| | | |
|---|---|---|
| gat gat att tta aaa cgc ttg tat gag ttg aag gca gca gtc gat ggc<br>Asp Asp Ile Leu Lys Arg Leu Tyr Glu Leu Lys Ala Ala Val Asp Gly<br>60                       65                   70                   75 | 302 |
| ctt tca aag atg att cac acc cca gat gca gac ttg gac gta acc aac<br>Leu Ser Lys Met Ile His Thr Pro Asp Ala Asp Leu Asp Val Thr Asn<br>                      80                   85                   90 | 350 |
| atc ctg caa gct gat gag ccc aca act tta gcc aca aac aca ttg gac<br>Ile Leu Gln Ala Asp Glu Pro Thr Thr Leu Ala Thr Asn Thr Leu Asp<br>                 95                  100                  105 | 398 |
| ttg aat tcc gtg ctt gga aag gac tat ggg gcg ctg aaa gac att gtg<br>Leu Asn Ser Val Leu Gly Lys Asp Tyr Gly Ala Leu Lys Asp Ile Val<br>          110                   115                  120 | 446 |
| atc aac gca aac cca gcc tcc cca cca ctg tcc ctg ctt gtg ctg cac<br>Ile Asn Ala Asn Pro Ala Ser Pro Pro Leu Ser Leu Leu Val Leu His<br>125                   130                  135 | 494 |
| agg ctg ctc tgt gaa cgc tac agg gtc ctg tcc act gtg cac aca cat<br>Arg Leu Leu Cys Glu Arg Tyr Arg Val Leu Ser Thr Val His Thr His<br>140                   145                  150               155 | 542 |
| tcg tct gtc aag aat gtg ccc gag aat ctt gtc aag tgc ttc ggg gag<br>Ser Ser Val Lys Asn Val Pro Glu Asn Leu Val Lys Cys Phe Gly Glu<br>                    160                  165                  170 | 590 |
| cag gct agg aag cag tcc cgc cac gag tat cag ctg ggc ttc act ctg<br>Gln Ala Arg Lys Gln Ser Arg His Glu Tyr Gln Leu Gly Phe Thr Leu<br>          175                   180                  185 | 638 |
| att tgg aag aat gtg ccc aag aca cag atg aag ttc agt gta caa acc<br>Ile Trp Lys Asn Val Pro Lys Thr Gln Met Lys Phe Ser Val Gln Thr<br>                    190                  195                  200 | 686 |
| atg tgc ccc att gaa gga gaa ggg aac atc gca cgt ttc ctg ttc tct<br>Met Cys Pro Ile Glu Gly Glu Gly Asn Ile Ala Arg Phe Leu Phe Ser<br>205                   210                  215 | 734 |
| ctg ttt ggc cag aag cat aat gct gtc acc ctc acc ctc atc gat agc<br>Leu Phe Gly Gln Lys His Asn Ala Val Thr Leu Thr Leu Ile Asp Ser<br>220                   225                  230               235 | 782 |
| tgg gtg gat atc gcc atg ttt cag ctt cga gaa ggc agc agt aaa gaa<br>Trp Val Asp Ile Ala Met Phe Gln Leu Arg Glu Gly Ser Ser Lys Glu<br>                    240                  245                  250 | 830 |
| aaa gcg gcc gtg ttc cgc tct atg aac tcc gct ttg ggg agg agc ccg<br>Lys Ala Ala Val Phe Arg Ser Met Asn Ser Ala Leu Gly Arg Ser Pro<br>          255                   260                  265 | 878 |
| tgg ctg gtt gga aat gag ctc act gtg gca gat gtg gtg ctg tgg tct<br>Trp Leu Val Gly Asn Glu Leu Thr Val Ala Asp Val Val Leu Trp Ser<br>                    270                  275                  280 | 926 |
| gtg ctc cag cag act ggg ggc agc agt ggg gca gca ccc acc aat gtg<br>Val Leu Gln Gln Thr Gly Gly Ser Ser Gly Ala Ala Pro Thr Asn Val<br>285                   290                  295 | 974 |
| cag cgg tgg ctt aag tcc tgt gaa aac ctg gcc ccc ttc agc act gcc<br>Gln Arg Trp Leu Lys Ser Cys Glu Asn Leu Ala Pro Phe Ser Thr Ala<br>300                   305                  310               315 | 1022 |
| ctt cag ctc ctt aag tga attcgagcag cttgtcttgc agggttcaac<br>Leu Gln Leu Leu Lys<br>          320 | 1070 |
| agaagaatgg tacggcttcc agtctgttgt cagaaaggga cttgtccaat aaagtaccat | 1130 |
| atcatctaaa aaaaaaaaaa aaaaaaaaaa aaaaaaaaaa aaaaaaaaaa aaaaaaaaaa | 1190 |
| aaaaaaaaaa aaaaaaaaaa aaaaaaaaaa aaaaaaaaaa aaa | 1233 |

<210> SEQ ID NO 5
<211> LENGTH: 320
<212> TYPE: PRT

<213> ORGANISM: Mus musculus

<400> SEQUENCE: 5

```
Met Pro Met Tyr Gln Val Lys Pro Tyr His Gly Gly Ser Ala Pro Leu
1               5                   10                  15

Arg Val Glu Leu Pro Thr Cys Met Tyr Arg Leu Pro Asn Val His Ser
            20                  25                  30

Lys Thr Thr Ser Pro Ala Thr Asp Ala Gly His Val Gln Glu Thr Ser
        35                  40                  45

Glu Pro Ser Leu Gln Ala Leu Glu Ser Arg Gln Asp Asp Ile Leu Lys
    50                  55                  60

Arg Leu Tyr Glu Leu Lys Ala Ala Val Asp Gly Leu Ser Lys Met Ile
65                  70                  75                  80

His Thr Pro Asp Ala Asp Leu Asp Val Thr Asn Ile Leu Gln Ala Asp
                85                  90                  95

Glu Pro Thr Thr Leu Ala Thr Asn Thr Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
    130                 135                 140

Arg Tyr Arg Val Leu Ser Thr Val His Thr His Ser Ser Val Lys Asn
145                 150                 155                 160

Val Pro Glu Asn Leu Val Lys Cys Phe Gly Glu Gln Ala Arg Lys Gln
                165                 170                 175

Ser Arg His Glu Tyr Gln Leu Gly Phe Thr Leu Ile Trp Lys Asn Val
            180                 185                 190

Pro Lys Thr Gln Met Lys Phe Ser Val Gln Thr Met Cys Pro Ile Glu
        195                 200                 205

Gly Glu Gly Asn Ile Ala Arg Phe Leu Phe Ser Leu Phe Gly Gln Lys
    210                 215                 220

His Asn Ala Val Thr Leu Thr Leu Ile Asp Ser Trp Val Asp Ile Ala
225                 230                 235                 240

Met Phe Gln Leu Arg Glu Gly Ser Ser Lys Glu Lys Ala Ala Val Phe
                245                 250                 255

Arg Ser Met Asn Ser Ala Leu Gly Arg Ser Pro Trp Leu Val Gly Asn
            260                 265                 270

Glu Leu Thr Val Ala Asp Val Val Leu Trp Ser Val Leu Gln Gln Thr
        275                 280                 285

Gly Gly Ser Ser Gly Ala Ala Pro Thr Asn Val Gln Arg Trp Leu Lys
    290                 295                 300

Ser Cys Glu Asn Leu Ala Pro Phe Ser Thr Ala Leu Gln Leu Leu Lys
305                 310                 315                 320
```

<210> SEQ ID NO 6
<211> LENGTH: 320
<212> TYPE: PRT
<213> ORGANISM: Mus musculus

<400> SEQUENCE: 6

```
Met Pro Met Tyr Gln Val Lys Pro Tyr His Gly Gly Ser Ala Pro Leu
1               5                   10                  15

Arg Val Glu Leu Pro Thr Cys Met Tyr Arg Leu Pro Asn Val His Ser
            20                  25                  30

Lys Thr Thr Ser Pro Ala Thr Asp Ala Gly His Val Gln Glu Thr Ser
```

|  | 35 |  |  | 40 |  |  |  | 45 |  |  |
|---|---|---|---|---|---|---|---|---|---|---|

Glu Pro Ser Leu Gln Ala Leu Glu Ser Arg Gln Asp Asp Ile Leu Lys
                50                  55                  60

Arg Leu Tyr Glu Leu Lys Ala Ala Val Asp Gly Leu Ser Lys Met Ile
 65                  70                  75                  80

His Thr Pro Asp Ala Asp Leu Asp Val Thr Asn Ile Leu Gln Ala Asp
                    85                  90                  95

Glu Pro Thr Thr Leu Ala Thr Asn Thr Leu Asp Leu Asn Ser Val Leu
                100                 105                 110

Gly Lys Asp Tyr Gly Ala Leu Lys Asp Ile Val Ile Asn Ala Asn Pro
                115                 120                 125

Ala Ser Pro Pro Leu Ser Leu Leu Val Leu His Arg Leu Leu Cys Glu
130                 135                 140

Arg Tyr Arg Val Leu Ser Thr Val His Thr His Ser Ser Val Lys Asn
145                 150                 155                 160

Val Pro Glu Asn Leu Val Lys Cys Phe Gly Glu Gln Ala Arg Lys Gln
                165                 170                 175

Ser Arg His Glu Tyr Gln Leu Gly Phe Thr Leu Ile Trp Lys Asn Val
                180                 185                 190

Pro Lys Thr Gln Met Lys Phe Ser Val Gln Thr Met Cys Pro Ile Glu
                195                 200                 205

Gly Glu Gly Asn Ile Ala Arg Phe Leu Phe Ser Leu Phe Gly Gln Lys
                210                 215                 220

His Asn Ala Val Thr Leu Thr Leu Ile Asp Ser Trp Val Asp Ile Ala
225                 230                 235                 240

Met Phe Gln Leu Arg Glu Gly Ser Ser Lys Glu Lys Ala Ala Val Phe
                245                 250                 255

Arg Ser Met Asn Ser Ala Leu Gly Arg Ser Pro Trp Leu Val Gly Asn
                260                 265                 270

Glu Leu Thr Val Ala Asp Val Val Leu Trp Ser Val Leu Gln Gln Thr
                275                 280                 285

Gly Gly Ser Ser Gly Ala Ala Pro Thr Asn Val Gln Arg Trp Leu Lys
                290                 295                 300

Ser Cys Glu Asn Leu Ala Pro Phe Ser Thr Ala Leu Gln Leu Leu Lys
305                 310                 315                 320

<210> SEQ ID NO 7
<211> LENGTH: 2960
<212> TYPE: DNA
<213> ORGANISM: Homo sapiens
<220> FEATURE:
<221> NAME/KEY: CDS
<222> LOCATION: (102)..(1499)

<400> SEQUENCE: 7

```
tccgggagga ttacccagga gaccgctggt gggaggcgcg gctggcgccg ctgcgcgcat      60
gggcctgttc ctggcccgca gccgccacct acccagtgac c atg ata gtg ttt gtc    116
                                             Met Ile Val Phe Val
                                              1               5 agg ttc aac tcc agc cat ggt ttc cca gtg gag gtc gat tct gac acc      164
Arg Phe Asn Ser Ser His Gly Phe Pro Val Glu Val Asp Ser Asp Thr
             10                  15                  20 agc atc ttc cag ctc aag gag gtg gtt gct aag cga cag ggg gtt ccg      212
Ser Ile Phe Gln Leu Lys Glu Val Val Ala Lys Arg Gln Gly Val Pro
         25                  30                  35 gct gac cag ttg cgt gtg att ttc gca ggg aag gag ctg agg aat gac      260
```

```
Ala Asp Gln Leu Arg Val Ile Phe Ala Gly Lys Glu Leu Arg Asn Asp
         40                  45                  50 tgg act gtg cag aat tgt gac ctg gat cag cag agc att gtt cac att         308
Trp Thr Val Gln Asn Cys Asp Leu Asp Gln Gln Ser Ile Val His Ile
 55                  60                  65 gtg cag aga ccg tgg aga aaa ggt caa gaa atg aat gca act gga ggc         356
Val Gln Arg Pro Trp Arg Lys Gly Gln Glu Met Asn Ala Thr Gly Gly
 70                  75                  80                  85 gac gac ccc aga aac gcg gcg gga ggc tgt gag cgg gag ccc cag agc         404
Asp Asp Pro Arg Asn Ala Ala Gly Gly Cys Glu Arg Glu Pro Gln Ser
                 90                  95                 100 ttg act cgg gtg gac ctc agc agc tca gtc ctc cca gga gac tct gtg         452
Leu Thr Arg Val Asp Leu Ser Ser Ser Val Leu Pro Gly Asp Ser Val
            105                 110                 115 ggg ctg gct gtc att ctg cac act gac agc agg aag gac tca cca cca         500
Gly Leu Ala Val Ile Leu His Thr Asp Ser Arg Lys Asp Ser Pro Pro
120                 125                 130 gct gga agt cca gca ggt aga tca atc tac aac agc ttt tat gtg tat         548
Ala Gly Ser Pro Ala Gly Arg Ser Ile Tyr Asn Ser Phe Tyr Val Tyr
        135                 140                 145 tgc aaa ggc ccc tgt caa aga gtg cag ccg gga aaa ctc agg gta cag         596
Cys Lys Gly Pro Cys Gln Arg Val Gln Pro Gly Lys Leu Arg Val Gln
150                 155                 160                 165 tgc agc acc tgc agg cag gca acg ctc acc ttg acc cag ggt cca tct         644
Cys Ser Thr Cys Arg Gln Ala Thr Leu Thr Leu Thr Gln Gly Pro Ser
            170                 175                 180 tgc tgg gat gat gtt tta att cca aac cgg atg agt ggt gaa tgc caa         692
Cys Trp Asp Asp Val Leu Ile Pro Asn Arg Met Ser Gly Glu Cys Gln
        185                 190                 195 tcc cca cac tgc cct ggg act agt gca gaa ttt ttc ttt aaa tgt gga         740
Ser Pro His Cys Pro Gly Thr Ser Ala Glu Phe Phe Phe Lys Cys Gly
200                 205                 210 gca cac ccc acc tct gac aag gaa aca cca gta gct ttg cac ctg atc         788
Ala His Pro Thr Ser Asp Lys Glu Thr Pro Val Ala Leu His Leu Ile
215                 220                 225 gca aca aat agt cgg aac atc act tgc att acg tgc aca gac gtc agg         836
Ala Thr Asn Ser Arg Asn Ile Thr Cys Ile Thr Cys Thr Asp Val Arg
230                 235                 240                 245 agc ccc gtc ctg gtt ttc cag tgc aac tcc cgc cac gtg att tgc tta         884
Ser Pro Val Leu Val Phe Gln Cys Asn Ser Arg His Val Ile Cys Leu
            250                 255                 260 gac tgt ttc cac tta tac tgt gtg aca aga ctc aat gat cgg cag ttt         932
Asp Cys Phe His Leu Tyr Cys Val Thr Arg Leu Asn Asp Arg Gln Phe
        265                 270                 275 gtt cac gac cct caa ctt ggc tac tcc ctg cct tgt gtg gct ggc tgt         980
Val His Asp Pro Gln Leu Gly Tyr Ser Leu Pro Cys Val Ala Gly Cys
            280                 285                 290 ccc aac tcc ttg att aaa gag ctc cat cac ttc agg att ctg gga gaa        1028
Pro Asn Ser Leu Ile Lys Glu Leu His His Phe Arg Ile Leu Gly Glu
295                 300                 305 gag cag tac aac cgg tac cag cag tat ggt gca gag gag tgt gtc ctg        1076
Glu Gln Tyr Asn Arg Tyr Gln Gln Tyr Gly Ala Glu Glu Cys Val Leu
310                 315                 320                 325 cag atg ggg ggc gtg tta tgc ccc cgc cct ggc tgt gga gcg ggg ctg        1124
Gln Met Gly Gly Val Leu Cys Pro Arg Pro Gly Cys Gly Ala Gly Leu
            330                 335                 340 ctg ccg gag cct gac cag agg aaa gtc acc tgc gaa ggg ggc aat ggc        1172
Leu Pro Glu Pro Asp Gln Arg Lys Val Thr Cys Glu Gly Gly Asn Gly
        345                 350                 355
```

```
ctg ggc tgt ggg ttt gcc ttc tgc cgg gaa tgt aaa gaa gcg tac cat      1220
Leu Gly Cys Gly Phe Ala Phe Cys Arg Glu Cys Lys Glu Ala Tyr His
        360                 365                 370 gaa ggg gag tgc agt gcc gta ttt gaa gcc tca gga aca act act cag      1268
Glu Gly Glu Cys Ser Ala Val Phe Glu Ala Ser Gly Thr Thr Thr Gln
    375                 380                 385 gcc tac aga gtc gat gaa aga gcc gcc gag cag gct cgt tgg gaa gca      1316
Ala Tyr Arg Val Asp Glu Arg Ala Ala Glu Gln Ala Arg Trp Glu Ala
390                 395                 400                 405 gcc tcc aaa gaa acc atc aag aaa acc acc aag ccc tgt ccc cgc tgc      1364
Ala Ser Lys Glu Thr Ile Lys Lys Thr Thr Lys Pro Cys Pro Arg Cys
                410                 415                 420 cat gta cca gtg gaa aaa aat gga ggc tgc atg cac atg aag tgt ccg      1412
His Val Pro Val Glu Lys Asn Gly Gly Cys Met His Met Lys Cys Pro
            425                 430                 435 cag ccc cag tgc agg ctc gag tgg tgc tgg aac tgt ggc tgc gag tgg      1460
Gln Pro Gln Cys Arg Leu Glu Trp Cys Trp Asn Cys Gly Cys Glu Trp
        440                 445                 450 aac cgc gtc tgc atg ggg gac cac tgg ttc gac gtg tag ccagggcggc      1509
Asn Arg Val Cys Met Gly Asp His Trp Phe Asp Val
    455                 460                 465 cgggcgcccc atcgccacat cctgggggag catacccagt gtctaccttc attttctaat   1569
tctcttttca acacacaca cacacgcgcg cgcgcgcaca cacactcttc aagtttttt    1629 caaagtccaa ctacagccaa attgcagaag aaactcctgg atcccttta ctatgtccat    1689 gaaaaacagc agagtaaaat tacagaagaa gctcctgaat ccctttcagt ttgtccacac   1749
aagacagcag agccatctgc gacaccacca acaggcgttc tcagcctccg gatgacacaa   1809 ataccgagc acagattcaa gtgcaatcca tgtatctgta tgggtcattc tcacctgaat    1869
tcgagacagg cagaatcagt agctggagag agagttctca catttaatat cctgccttt    1929 accttcagta acaccatga agatgccatt gacaaggtgt ttctctgtaa aatgaactgc    1989
agtgggttct ccaaactaga ttcatggctt taacagtaat gttcttattt aaattttcag   2049
aaagcatcta ttcccaaaga accccaggca atagtcaaaa acatttgttt atccttaaga   2109
attccatcta tataaatcgc attaatcgaa ataccaacta tgtgtaaatc aacttgtcac   2169
aaagtgagaa attatgaaag ttaatttgaa tgttgaatgt ttgaattaca gggaagaaat   2229
caagttaatg tactttcatt cccttcatg atttgcaact ttagaaagaa attgtttttc    2289
tgaaagtatc accaaaaaat ctatagtttg attctgagta ttcattttgc aacttggaga   2349
ttttgctaat acatttggct ccactgtaaa tttaatagat aaagtgccta taaaggaaac    2409
acgtttagaa atgatttcaa aatgatattc aatcttaaca aaagtgaaca ttattaaatc    2469
agaatcttta aagaggagcc tttccagaac taccaaaatg aagacacgcc cgactctctc   2529
catcagaagg gtttataccc ctttggcaca ccctctctgt ccaatctgca agtcccaggg   2589
agctctgcat accagggggtt ccccaggaga gaccttctct taggacagta aactcactag   2649
aatattcctt atgttgacat ggattggatt tcagttcaat caaactttca gcttttttt    2709 cagccattca caacacaatc aaaagattaa caacactgca tgcggcaaac cgcatgctct   2769
tacccacact acgcagaaga gaaagtacaa ccactatctt ttgttctacc tgtattgtct   2829
gacttctcag gaagatcgtg aacataactg agggcatgag tctcactagc acatggaggc   2889
ccttttggat ttagagactg taaattatta aatcggcaac agggcttctc ttttagatg    2949 tagcactgaa a                                                        2960
```

<210> SEQ ID NO 8
<211> LENGTH: 465
<212> TYPE: PRT
<213> ORGANISM: Homo sapiens

<400> SEQUENCE: 8

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Pro Val
    210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285

Cys Val Ala Gly Cys Pro Asn Ser Leu Ile Lys Glu Leu His His Phe
    290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
        355                 360                 365

Lys Glu Ala Tyr His Glu Gly Glu Cys Ser Ala Val Phe Glu Ala Ser
    370                 375                 380

```
Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
            405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
            435                 440                 445

Cys Gly Cys Glu Trp Asn Arg Val Cys Met Gly Asp His Trp Phe Asp
            450                 455                 460

Val
465

<210> SEQ ID NO 9
<211> LENGTH: 465
<212> TYPE: PRT
<213> ORGANISM: Homo sapiens

<400> SEQUENCE: 9

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Pro Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285
```

```
Cys Val Ala Gly Cys Pro Asn Ser Leu Ile Lys Glu Leu His His Phe
    290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
        355                 360                 365

Lys Glu Ala Tyr His Glu Gly Glu Cys Ser Ala Val Phe Glu Ala Ser
    370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
        435                 440                 445

Cys Gly Cys Glu Trp Asn Arg Val Cys Met Gly Asp His Trp Phe Asp
    450                 455                 460

Val
465

<210> SEQ ID NO 10
<211> LENGTH: 471
<212> TYPE: DNA
<213> ORGANISM: Homo sapiens
<220> FEATURE:
<221> NAME/KEY: CDS
<222> LOCATION: (1)..(471)

<400> SEQUENCE: 10 gga agt cca gca ggt aga tca atc tac aac agc ttt tat gtg tat tgc       48
Gly Ser Pro Ala Gly Arg Ser Ile Tyr Asn Ser Phe Tyr Val Tyr Cys
1               5                   10                  15 aaa ggc ccc tgt caa aga gtg cag ccg gga aaa ctc agg gta cag tgc       96
Lys Gly Pro Cys Gln Arg Val Gln Pro Gly Lys Leu Arg Val Gln Cys
            20                  25                  30 agc acc tgc agg cag gca acg ctc acc ttg acc cag ggt cca tct tgc      144
Ser Thr Cys Arg Gln Ala Thr Leu Thr Leu Thr Gln Gly Pro Ser Cys
        35                  40                  45 tgg gat gat gtt tta att cca aac cgg atg agt ggt gaa tgc caa tcc      192
Trp Asp Asp Val Leu Ile Pro Asn Arg Met Ser Gly Glu Cys Gln Ser
50                  55                  60 cca cac tgc cct ggg act agt gca gaa ttt ttc ttt aaa tgt gga gca      240
Pro His Cys Pro Gly Thr Ser Ala Glu Phe Phe Phe Lys Cys Gly Ala
65                  70                  75                  80 cac ccc acc tct gac aag gaa aca tca gta gct ttg cac ctg atc gca      288
His Pro Thr Ser Asp Lys Glu Thr Ser Val Ala Leu His Leu Ile Ala
                85                  90                  95 aca aat agt cgg aac atc act tgc att acg tgc aca gac gtc agg agc      336
Thr Asn Ser Arg Asn Ile Thr Cys Ile Thr Cys Thr Asp Val Arg Ser
            100                 105                 110 ccc gtc ctg gtt ttc cag tgc aac tcc cgc cac gtg att tgc tta gac      384
Pro Val Leu Val Phe Gln Cys Asn Ser Arg His Val Ile Cys Leu Asp
        115                 120                 125
```

```
tgt ttc cac tta tac tgt gtg aca aga ctc aat gat cgg cag ttt gtt    432
Cys Phe His Leu Tyr Cys Val Thr Arg Leu Asn Asp Arg Gln Phe Val
    130                 135                 140 cac gac cct caa ctt ggc tac tcc ctg cct tgt gtg tag                471
His Asp Pro Gln Leu Gly Tyr Ser Leu Pro Cys Val
145                 150                 155
```

<210> SEQ ID NO 11
<211> LENGTH: 156
<212> TYPE: PRT
<213> ORGANISM: Homo sapiens

<400> SEQUENCE: 11

```
Gly Ser Pro Ala Gly Arg Ser Ile Tyr Asn Ser Phe Tyr Val Tyr Cys
1               5                   10                  15

Lys Gly Pro Cys Gln Arg Val Gln Pro Gly Lys Leu Arg Val Gln Cys
            20                  25                  30

Ser Thr Cys Arg Gln Ala Thr Leu Thr Leu Thr Gln Gly Pro Ser Cys
        35                  40                  45

Trp Asp Asp Val Leu Ile Pro Asn Arg Met Ser Gly Glu Cys Gln Ser
 50                  55                  60

Pro His Cys Pro Gly Thr Ser Ala Glu Phe Phe Lys Cys Gly Ala
65                  70                  75                  80

His Pro Thr Ser Asp Lys Glu Thr Ser Val Ala Leu His Leu Ile Ala
                85                  90                  95

Thr Asn Ser Arg Asn Ile Thr Cys Ile Thr Cys Thr Asp Val Arg Ser
            100                 105                 110

Pro Val Leu Val Phe Gln Cys Asn Ser Arg His Val Ile Cys Leu Asp
        115                 120                 125

Cys Phe His Leu Tyr Cys Val Thr Arg Leu Asn Asp Arg Gln Phe Val
    130                 135                 140

His Asp Pro Gln Leu Gly Tyr Ser Leu Pro Cys Val
145                 150                 155
```

<210> SEQ ID NO 12
<211> LENGTH: 156
<212> TYPE: PRT
<213> ORGANISM: Homo sapiens

<400> SEQUENCE: 12

```
Gly Ser Pro Ala Gly Arg Ser Ile Tyr Asn Ser Phe Tyr Val Tyr Cys
1               5                   10                  15

Lys Gly Pro Cys Gln Arg Val Gln Pro Gly Lys Leu Arg Val Gln Cys
            20                  25                  30

Ser Thr Cys Arg Gln Ala Thr Leu Thr Leu Thr Gln Gly Pro Ser Cys
        35                  40                  45

Trp Asp Asp Val Leu Ile Pro Asn Arg Met Ser Gly Glu Cys Gln Ser
 50                  55                  60

Pro His Cys Pro Gly Thr Ser Ala Glu Phe Phe Lys Cys Gly Ala
65                  70                  75                  80

His Pro Thr Ser Asp Lys Glu Thr Ser Val Ala Leu His Leu Ile Ala
                85                  90                  95

Thr Asn Ser Arg Asn Ile Thr Cys Ile Thr Cys Thr Asp Val Arg Ser
            100                 105                 110

Pro Val Leu Val Phe Gln Cys Asn Ser Arg His Val Ile Cys Leu Asp
        115                 120                 125
```

```
Cys Phe His Leu Tyr Cys Val Thr Arg Leu Asn Asp Arg Gln Phe Val
        130                 135                 140

His Asp Pro Gln Leu Gly Tyr Ser Leu Pro Cys Val
145                 150                 155

<210> SEQ ID NO 13
<211> LENGTH: 1470
<212> TYPE: DNA
<213> ORGANISM: Rattus norvegicus
<220> FEATURE:
<221> NAME/KEY: CDS
<222> LOCATION: (1)..(1470)

<400> SEQUENCE: 13 atg ata gtg ttt gtc agg ttc aac tcc agc tat ggc ttc cca gtg gag      48
Met Ile Val Phe Val Arg Phe Asn Ser Ser Tyr Gly Phe Pro Val Glu
1               5                   10                  15 gtc gat tct gac acc agc atc ttc cag ctc aag gaa gtg gtt gct aag      96
Val Asp Ser Asp Thr Ser Ile Phe Gln Leu Lys Glu Val Val Ala Lys
                20                  25                  30 cga cag ggg gtt cca gct gac cag ctg cga gtg att ttt gct ggg aag     144
Arg Gln Gly Val Pro Ala Asp Gln Leu Arg Val Ile Phe Ala Gly Lys
            35                  40                  45 gag ctg cag aat cac ctg aca gta cag cat ccc cag gat ggt ttc tgt     192
Glu Leu Gln Asn His Leu Thr Val Gln His Pro Gln Asp Gly Phe Cys
        50                  55                  60 cat aag tct cac ctt gct gtt cat aat ctc tct cag cag gac gtc aca     240
His Lys Ser His Leu Ala Val His Asn Leu Ser Gln Gln Asp Val Thr
65                  70                  75                  80 cag aac tgt gac ctg gaa caa cag agt atc gtt cac ata gta cag aga     288
Gln Asn Cys Asp Leu Glu Gln Gln Ser Ile Val His Ile Val Gln Arg
                85                  90                  95 cca cag agg aaa agt cac gaa aca aat gcc tct gga ggg gac aaa ccc     336
Pro Gln Arg Lys Ser His Glu Thr Asn Ala Ser Gly Gly Asp Lys Pro
            100                 105                 110 cag agc acc ccg gag ggc tcc ata tgg gag ccc aga agc ttg act cga     384
Gln Ser Thr Pro Glu Gly Ser Ile Trp Glu Pro Arg Ser Leu Thr Arg
        115                 120                 125 gtg gac ctc agc agc cat atc ctg cca gcg gac tcc gtg ggg ctg gca     432
Val Asp Leu Ser Ser His Ile Leu Pro Ala Asp Ser Val Gly Leu Ala
130                 135                 140 gtc att ctg gac aca gac agc aag agt gac tca gaa gca gcc aga ggt     480
Val Ile Leu Asp Thr Asp Ser Lys Ser Asp Ser Glu Ala Ala Arg Gly
145                 150                 155                 160 cca gaa gct aaa ccc acc tac cac agc ttt ttt gtc tac tgc aaa ggc     528
Pro Glu Ala Lys Pro Thr Tyr His Ser Phe Phe Val Tyr Cys Lys Gly
                165                 170                 175 ccc tgc cac aag gtc cag cct ggg aaa ctc cga gtt cag tgc ggc acc     576
Pro Cys His Lys Val Gln Pro Gly Lys Leu Arg Val Gln Cys Gly Thr
            180                 185                 190 tgc aga caa gca acc ctc acc ttg gcc cag ggc cca tct tgc tgg gat     624
Cys Arg Gln Ala Thr Leu Thr Leu Ala Gln Gly Pro Ser Cys Trp Asp
        195                 200                 205 gat gtc tta att cca aac cgg atg agt gga gag tgt caa tct cca gac     672
Asp Val Leu Ile Pro Asn Arg Met Ser Gly Glu Cys Gln Ser Pro Asp
210                 215                 220 tgc cct ggg aca aga gct gaa ttt ttc ttt aaa tgt gga gca cac cca     720
Cys Pro Gly Thr Arg Ala Glu Phe Phe Phe Lys Cys Gly Ala His Pro
225                 230                 235                 240 acc tca gac aag gac aca tca gta gct ttg aac ctg atc acc aac aac     768
Thr Ser Asp Lys Asp Thr Ser Val Ala Leu Asn Leu Ile Thr Asn Asn
```

```
                245                 250                 255
agc cgc agc atc ccc tgc atc gcg tgc acg gat gtc agg aac cct gtc         816
Ser Arg Ser Ile Pro Cys Ile Ala Cys Thr Asp Val Arg Asn Pro Val
            260                 265                 270 ttg gtc ttc caa tgt aac cac cgc cac gtg atc tgt ttg gac tgc ttc         864
Leu Val Phe Gln Cys Asn His Arg His Val Ile Cys Leu Asp Cys Phe
        275                 280                 285 cac ttg tac tgt gtc aca agg ctc aac gat cgg cag ttt gtc cac gac         912
His Leu Tyr Cys Val Thr Arg Leu Asn Asp Arg Gln Phe Val His Asp
    290                 295                 300 gct cag ctt ggc tac tcg ctg ccg tgt gtg gct ggc tgt ccc aac tcc         960
Ala Gln Leu Gly Tyr Ser Leu Pro Cys Val Ala Gly Cys Pro Asn Ser
305                 310                 315                 320 ctg att aaa gag ctc cat cac ttc agg atc ctt gga gaa gag cag tac        1008
Leu Ile Lys Glu Leu His His Phe Arg Ile Leu Gly Glu Glu Gln Tyr
            325                 330                 335 aac agg tac cag cag tat ggt gcc gag gag tgc gtg ctg cag atg gga        1056
Asn Arg Tyr Gln Gln Tyr Gly Ala Glu Glu Cys Val Leu Gln Met Gly
        340                 345                 350 ggt gtg ctg tgc ccc cgt cct ggc tgc gga gct ggg ctg ctg cct gaa        1104
Gly Val Leu Cys Pro Arg Pro Gly Cys Gly Ala Gly Leu Leu Pro Glu
    355                 360                 365 cag ggc cag aag aaa gtc acc tgt gaa ggg ggc aac ggc ctg ggc tgt        1152
Gln Gly Gln Lys Lys Val Thr Cys Glu Gly Gly Asn Gly Leu Gly Cys
370                 375                 380 ggg ttc gtt ttc tgc cgg gac tgc aag gaa gca tac cat gaa ggg gag        1200
Gly Phe Val Phe Cys Arg Asp Cys Lys Glu Ala Tyr His Glu Gly Glu
            385                 390                 395                 400 tgc gac tcg atg ttc gaa gcc tcg ggg gcg act tct cag gca tac cgg        1248
Cys Asp Ser Met Phe Glu Ala Ser Gly Ala Thr Ser Gln Ala Tyr Arg
                405                 410                 415 gtg gat caa aga gct gct gag caa gca cgg tgg gag gag gcc tcc aag        1296
Val Asp Gln Arg Ala Ala Glu Gln Ala Arg Trp Glu Glu Ala Ser Lys
            420                 425                 430 gaa acc atc aag aaa acc acc aag cct tgt cct cgc tgc aat gtg ccc        1344
Glu Thr Ile Lys Lys Thr Thr Lys Pro Cys Pro Arg Cys Asn Val Pro
        435                 440                 445 att gaa aag aat gga gga tgt atg cac atg aag tgt cct cag ccc cag        1392
Ile Glu Lys Asn Gly Gly Cys Met His Met Lys Cys Pro Gln Pro Gln
    450                 455                 460 tgc aag ctg gag tgg tgt tgg aac tgc ggc tgt gag tgg aac cga gcc        1440
Cys Lys Leu Glu Trp Cys Trp Asn Cys Gly Cys Glu Trp Asn Arg Ala
465                 470                 475                 480 tgc atg ggt gat cac tgg ttt gac gtg tag                                1470
Cys Met Gly Asp His Trp Phe Asp Val
                485
```

<210> SEQ ID NO 14
<211> LENGTH: 489
<212> TYPE: PRT
<213> ORGANISM: Rattus norvegicus

<400> SEQUENCE: 14

```
Met Ile Val Phe Val Arg Phe Asn Ser Ser Tyr Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45
```

-continued

```
Glu Leu Gln Asn His Leu Thr Val Gln His Pro Gln Asp Gly Phe Cys
 50                  55                  60

His Lys Ser His Leu Ala Val His Asn Leu Ser Gln Gln Asp Val Thr
 65                  70                  75                  80

Gln Asn Cys Asp Leu Glu Gln Gln Ser Ile Val His Ile Val Gln Arg
                 85                  90                  95

Pro Gln Arg Lys Ser His Glu Thr Asn Ala Ser Gly Gly Asp Lys Pro
            100                 105                 110

Gln Ser Thr Pro Glu Gly Ser Ile Trp Glu Pro Arg Ser Leu Thr Arg
        115                 120                 125

Val Asp Leu Ser Ser His Ile Leu Pro Ala Asp Ser Val Gly Leu Ala
130                 135                 140

Val Ile Leu Asp Thr Asp Ser Lys Ser Asp Ser Glu Ala Ala Arg Gly
145                 150                 155                 160

Pro Glu Ala Lys Pro Thr Tyr His Ser Phe Phe Val Tyr Cys Lys Gly
                165                 170                 175

Pro Cys His Lys Val Gln Pro Gly Lys Leu Arg Val Gln Cys Gly Thr
            180                 185                 190

Cys Arg Gln Ala Thr Leu Thr Leu Ala Gln Gly Pro Ser Cys Trp Asp
        195                 200                 205

Asp Val Leu Ile Pro Asn Arg Met Ser Gly Glu Cys Gln Ser Pro Asp
210                 215                 220

Cys Pro Gly Thr Arg Ala Glu Phe Phe Lys Cys Gly Ala His Pro
225                 230                 235                 240

Thr Ser Asp Lys Asp Thr Ser Val Ala Leu Asn Leu Ile Thr Asn Asn
                245                 250                 255

Ser Arg Ser Ile Pro Cys Ile Ala Cys Thr Asp Val Arg Asn Pro Val
            260                 265                 270

Leu Val Phe Gln Cys Asn His Arg His Val Ile Cys Leu Asp Cys Phe
        275                 280                 285

His Leu Tyr Cys Val Thr Arg Leu Asn Asp Arg Gln Phe Val His Asp
290                 295                 300

Ala Gln Leu Gly Tyr Ser Leu Pro Cys Val Ala Gly Cys Pro Asn Ser
305                 310                 315                 320

Leu Ile Lys Glu Leu His His Phe Arg Ile Leu Gly Glu Glu Gln Tyr
                325                 330                 335

Asn Arg Tyr Gln Gln Tyr Gly Ala Glu Glu Cys Val Leu Gln Met Gly
            340                 345                 350

Gly Val Leu Cys Pro Arg Pro Gly Cys Gly Ala Gly Leu Leu Pro Glu
        355                 360                 365

Gln Gly Gln Lys Lys Val Thr Cys Glu Gly Gly Asn Gly Leu Gly Cys
370                 375                 380

Gly Phe Val Phe Cys Arg Asp Cys Lys Glu Ala Tyr His Glu Gly Glu
385                 390                 395                 400

Cys Asp Ser Met Phe Glu Ala Ser Gly Ala Thr Ser Gln Ala Tyr Arg
                405                 410                 415

Val Asp Gln Arg Ala Ala Glu Gln Ala Arg Trp Glu Ala Ser Lys
            420                 425                 430

Glu Thr Ile Lys Lys Thr Thr Lys Pro Cys Pro Arg Cys Asn Val Pro
        435                 440                 445

Ile Glu Lys Asn Gly Gly Cys Met His Met Lys Cys Pro Gln Pro Gln
450                 455                 460

Cys Lys Leu Glu Trp Cys Trp Asn Cys Gly Cys Glu Trp Asn Arg Ala
```

```
                465                 470                 475                 480
Cys Met Gly Asp His Trp Phe Asp Val
                485

<210> SEQ ID NO 15
<211> LENGTH: 489
<212> TYPE: PRT
<213> ORGANISM: Rattus norvegicus

<400> SEQUENCE: 15

Met Ile Val Phe Val Arg Phe Asn Ser Ser Tyr Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Gln Asn His Leu Thr Val Gln His Pro Gln Asp Gly Phe Cys
    50                  55                  60

His Lys Ser His Leu Ala Val His Asn Leu Ser Gln Gln Asp Val Thr
65                  70                  75                  80

Gln Asn Cys Asp Leu Glu Gln Gln Ser Ile Val His Ile Val Gln Arg
                85                  90                  95

Pro Gln Arg Lys Ser His Glu Thr Asn Ala Ser Gly Gly Asp Lys Pro
            100                 105                 110

Gln Ser Thr Pro Glu Gly Ser Ile Trp Glu Pro Arg Ser Leu Thr Arg
        115                 120                 125

Val Asp Leu Ser Ser His Ile Leu Pro Ala Asp Ser Val Gly Leu Ala
    130                 135                 140

Val Ile Leu Asp Thr Asp Ser Lys Ser Asp Ser Glu Ala Ala Arg Gly
145                 150                 155                 160

Pro Glu Ala Lys Pro Thr Tyr His Ser Phe Phe Val Tyr Cys Lys Gly
                165                 170                 175

Pro Cys His Lys Val Gln Pro Gly Lys Leu Arg Val Gln Cys Gly Thr
            180                 185                 190

Cys Arg Gln Ala Thr Leu Thr Leu Ala Gln Gly Pro Ser Cys Trp Asp
        195                 200                 205

Asp Val Leu Ile Pro Asn Arg Met Ser Gly Glu Cys Gln Ser Pro Asp
    210                 215                 220

Cys Pro Gly Thr Arg Ala Glu Phe Phe Phe Lys Cys Gly Ala His Pro
225                 230                 235                 240

Thr Ser Asp Lys Asp Thr Ser Val Ala Leu Asn Leu Ile Thr Asn Asn
                245                 250                 255

Ser Arg Ser Ile Pro Cys Ile Ala Cys Thr Asp Val Arg Asn Pro Val
            260                 265                 270

Leu Val Phe Gln Cys Asn His Arg His Val Ile Cys Leu Asp Cys Phe
        275                 280                 285

His Leu Tyr Cys Val Thr Arg Leu Asn Asp Arg Gln Phe Val His Asp
    290                 295                 300

Ala Gln Leu Gly Tyr Ser Leu Pro Cys Val Ala Gly Cys Pro Asn Ser
305                 310                 315                 320

Leu Ile Lys Glu Leu His His Phe Arg Ile Leu Gly Glu Glu Gln Tyr
                325                 330                 335

Asn Arg Tyr Gln Gln Tyr Gly Ala Glu Glu Cys Val Leu Gln Met Gly
            340                 345                 350
```

```
Gly Val Leu Cys Pro Arg Pro Cys Gly Ala Gly Leu Leu Pro Glu
            355                 360                 365

Gln Gly Gln Lys Lys Val Thr Cys Glu Gly Gly Asn Gly Leu Gly Cys
        370                 375                 380

Gly Phe Val Phe Cys Arg Asp Cys Lys Glu Ala Tyr His Glu Gly Glu
385                 390                 395                 400

Cys Asp Ser Met Phe Glu Ala Ser Gly Ala Thr Ser Gln Ala Tyr Arg
                405                 410                 415

Val Asp Gln Arg Ala Ala Glu Gln Ala Arg Trp Glu Ala Ser Lys
                420                 425                 430

Glu Thr Ile Lys Lys Thr Thr Lys Pro Cys Pro Arg Cys Asn Val Pro
            435                 440                 445

Ile Glu Lys Asn Gly Gly Cys Met His Met Lys Cys Pro Gln Pro Gln
        450                 455                 460

Cys Lys Leu Glu Trp Cys Trp Asn Cys Gly Cys Glu Trp Asn Arg Ala
465                 470                 475                 480

Cys Met Gly Asp His Trp Phe Asp Val
                485
```

```
<210> SEQ ID NO 16
<211> LENGTH: 27
<212> TYPE: DNA
<213> ORGANISM: Homo sapiens

<400> SEQUENCE: 16
ttaagaattc ggaagtccag caggtag                                        27

<210> SEQ ID NO 17
<211> LENGTH: 29
<212> TYPE: DNA
<213> ORGANISM: Homo sapiens

<400> SEQUENCE: 17
attaggatcc ctacacacaa ggcagggag                                      29

<210> SEQ ID NO 18
<211> LENGTH: 19
<212> TYPE: DNA
<213> ORGANISM: Homo sapiens

<400> SEQUENCE: 18
gcgtttggaa tcactacag                                                 19

<210> SEQ ID NO 19
<211> LENGTH: 16
<212> TYPE: DNA
<213> ORGANISM: Homo sapiens

<400> SEQUENCE: 19
atgccgatgt accagg                                                    16

<210> SEQ ID NO 20
<211> LENGTH: 19
<212> TYPE: DNA
<213> ORGANISM: Homo sapiens

<400> SEQUENCE: 20
gggattcact ttaatttgg                                                 19

<210> SEQ ID NO 21
```

```
<211> LENGTH: 18
<212> TYPE: DNA
<213> ORGANISM: Homo sapiens

<400> SEQUENCE: 21
aatgttccct tcgccttc                                                   18

<210> SEQ ID NO 22
<211> LENGTH: 17
<212> TYPE: DNA
<213> ORGANISM: Homo sapiens

<400> SEQUENCE: 22
ttaaaaagga gccaggt                                                    17
```